US011083786B2

(12) United States Patent
Kamrud et al.

(10) Patent No.: US 11,083,786 B2
(45) Date of Patent: Aug. 10, 2021

(54) INDUCE AND ENHANCE IMMUNE RESPONSES USING RECOMBINANT REPLICON SYSTEMS

(71) Applicant: Janssen Pharmaceuticals, Inc., Titusville, NJ (US)

(72) Inventors: Kurt Iver Kamrud, San Diego, CA (US); Nathaniel Stephen Wang, San Diego, CA (US); Parinaz Aliahmad, San Diego, CA (US); Jason DeHart, San Diego, CA (US)

(73) Assignee: JANSSEN PHARMACEUTICALS, INC., Titusville, NJ (US)

( * ) Notice: Subject to any disclaimer, the term of this patent is extended or adjusted under 35 U.S.C. 154(b) by 8 days.

(21) Appl. No.: 16/251,928

(22) Filed: Jan. 18, 2019

(65) Prior Publication Data

US 2019/0224299 A1    Jul. 25, 2019

Related U.S. Application Data

(60) Provisional application No. 62/619,540, filed on Jan. 19, 2018.

(51) Int. Cl.
| | |
|---|---|
| *A61K 39/12* | (2006.01) |
| *C12N 15/113* | (2010.01) |
| *A61P 31/14* | (2006.01) |
| *C12N 15/62* | (2006.01) |
| *A61P 31/16* | (2006.01) |
| *A61K 39/00* | (2006.01) |

(52) U.S. Cl.
CPC .............. *A61K 39/12* (2013.01); *A61P 31/14* (2018.01); *A61P 31/16* (2018.01); *C12N 15/113* (2013.01); *C12N 15/62* (2013.01); *A61K 2039/53* (2013.01); *A61K 2039/545* (2013.01); *A61K 2039/552* (2013.01); *C12N 2760/16134* (2013.01); *C12N 2770/20043* (2013.01); *C12N 2770/36143* (2013.01)

(58) Field of Classification Search
None
See application file for complete search history.

(56) References Cited

U.S. PATENT DOCUMENTS

| | | | |
|---|---|---|---|
| 4,727,138 A | 2/1988 | Goeddel | |
| 4,738,927 A | 4/1988 | Taniguchi | |
| 4,762,791 A | 8/1988 | Goeddel | |
| 4,810,643 A | 3/1989 | Souza | |
| 4,892,743 A | 1/1990 | Leibowitz | |
| 4,966,843 A | 10/1990 | McCormick | |
| 4,999,291 A | 3/1991 | Souza | |
| 5,017,691 A | 5/1991 | Lee | |
| 5,116,742 A | 5/1992 | Cech | |
| 5,225,337 A | 7/1993 | Robertson | |
| 5,246,921 A | 9/1993 | Reddy | |
| 5,780,036 A | 7/1998 | Chisari | |
| 5,958,060 A | 9/1999 | Premerlani | |
| 6,041,252 A | 3/2000 | Walker | |
| 6,110,161 A | 8/2000 | Mathiesen | |
| 6,117,660 A | 9/2000 | Walters | |
| 6,224,879 B1 | 5/2001 | Sjoeberg | |
| 6,261,281 B1 | 7/2001 | Mathiesen | |
| 6,273,525 B1 | 8/2001 | Erban | |
| 6,278,895 B1 | 8/2001 | Bernard | |
| 6,319,901 B1 | 11/2001 | Bernard | |
| 6,697,669 B2 | 2/2004 | Dev | |
| 6,873,549 B2 | 3/2005 | Khalid | |
| 6,873,849 B2 | 3/2005 | De La Red | |
| 6,912,417 B1 | 6/2005 | Bernard | |
| 6,939,862 B2 | 9/2005 | Bureau | |
| 6,958,060 B2 | 10/2005 | Mathiesen | |
| 6,982,087 B2 | 1/2006 | Johnston | |
| 7,328,064 B2 | 2/2008 | Mathiesen | |
| 7,419,674 B2 | 9/2008 | Chulay | |
| 7,664,545 B2 | 2/2010 | Westersten | |
| 8,080,255 B2 | 12/2011 | Smith | |
| 8,187,249 B2 | 5/2012 | Bernard | |
| 8,209,006 B2 | 6/2012 | Smith | |
| 8,216,589 B2 | 7/2012 | Yum | |
| 8,859,198 B2 | 10/2014 | Bartholomeusz | |
| 8,961,995 B2* | 2/2015 | Frolov | A61K 39/12 424/218.1 |
| 9,364,664 B2 | 6/2016 | Masterson | |
| 9,452,285 B2 | 9/2016 | Draghia-Akli | |
| 9,801,897 B2 | 10/2017 | Geall | |
| 9,802,035 B2 | 10/2017 | Masterson | |

(Continued)

FOREIGN PATENT DOCUMENTS

| | | |
|---|---|---|
| WO | 8502862 | 7/1985 |
| WO | 8504188 | 9/1985 |

(Continued)

OTHER PUBLICATIONS

Frolov et al, (Journal of Virology, 1999, p. 3854-3865).*
Bolz et al.: "*Use of Recombinant Virus Replicon Particles for Vaccination against Mycobacterium ulcerans Disease*"; PLoS Negl Trop Dis., Aug. 14, 2015, vol. 9(8):e0004011., PDF File: p. 1-18.
International Search Report dated Apr. 23, 2019, regarding PCT/US2019/014210.
Lundstrom, Kenneth L.: "*Replicon RNA Viral Vectors as Vaccines*"; Vaccines, 2016, vol. 4(4). pii: E39. PDF File: p. 1-23.
Uematsu et al.: "*Lack of Interference with Immunogenicity of a Chimeric Alphavirus Replicon Particle-Based Influenza Vaccine by Preexisting Antivector Immunity*"; . Clin Vaccine Immunol., Jul. 2012, vol. 19(7), p. 991-998.

(Continued)

*Primary Examiner* — Agnieszka Boesen
(74) *Attorney, Agent, or Firm* — Ice Miller LLP

(57) ABSTRACT

The present disclosure generally relates to the use of different self-amplifying RNA molecules to enhance immune responses, for example immune responses following prophylactic vaccination or therapeutic administration. Some embodiments relate to compositions and methods for inducing an immune response in a subject using prime-boost immunization regimens.

24 Claims, 3 Drawing Sheets

Specification includes a Sequence Listing.

(56) References Cited

U.S. PATENT DOCUMENTS

| | | | |
|---|---|---|---|
| 10,538,786 B2* | 1/2020 | Kamrud | A61P 35/00 |
| 2004/0213805 A1* | 10/2004 | Verheije | C07K 14/005 |
| | | | 424/199.1 |
| 2004/0235133 A1 | 11/2004 | Frolov | |
| 2005/0070700 A1 | 3/2005 | Giese | |
| 2005/0277605 A1 | 12/2005 | Wu et al. | |
| 2009/0018031 A1 | 1/2009 | Trinklein | |
| 2009/0075384 A1 | 3/2009 | Kamrud | |
| 2011/0110974 A1 | 5/2011 | Depla | |
| 2012/0121650 A1 | 5/2012 | Johnston | |
| 2014/0079734 A1 | 3/2014 | Frolov | |
| 2016/0166678 A1 | 6/2016 | Kallen | |
| 2016/0362472 A1 | 12/2016 | Bitter | |
| 2017/0314043 A1 | 11/2017 | Kamrud | |
| 2018/0104359 A1 | 4/2018 | Kamrud | |
| 2018/0171340 A1 | 6/2018 | Kamrud | |

FOREIGN PATENT DOCUMENTS

| | | |
|---|---|---|
| WO | 9006370 | 6/1990 |
| WO | 9503777 A1 | 2/1995 |
| WO | 9531565 | 11/1995 |
| WO | 9637616 | 11/1996 |
| WO | 200224224 A2 | 3/2002 |
| WO | 2002042480 A2 | 5/2002 |
| WO | 2004055161 A2 | 7/2004 |
| WO | 2005087311 A1 | 9/2005 |
| WO | 2008093976 A1 | 8/2008 |
| WO | 2011015656 A2 | 2/2011 |
| WO | 2012087983 A1 | 6/2012 |
| WO | 2012109668 A1 | 8/2012 |
| WO | 2013007772 A1 | 1/2013 |
| WO | 2014170493 A2 | 10/2014 |
| WO | 2016020538 A1 | 2/2016 |
| WO | 2016054003 A1 | 4/2016 |
| WO | 2016184822 A1 | 11/2016 |
| WO | 2017024000 A1 | 2/2017 |
| WO | 2017172838 A1 | 10/2017 |
| WO | 2017176319 A1 | 10/2017 |
| WO | 2017180770 A1 | 10/2017 |
| WO | 2018075235 A1 | 4/2018 |
| WO | 2018106615 A1 | 6/2018 |

OTHER PUBLICATIONS

Xu et al.: "Type-specific and cross-reactive antibodies induced by human papillomavirus 31 L1/L2 virus-like particle";. J Med Microbiol. 2007, vol. 56(Pt 7), p. 907-913.
Boukhebza et al., "Comparative analysis of immunization schedules using a novel adenovirus-based immunotherapeutic targeting hepatitis B in naive and tolerant mouse models" Vaccine, 32(26), pp. 3258-3263, 2014.
Jones et al., "Hepatitis B virus reverse transcriptase: diverse functions as classical and emerging targets for antiviral intervention", Emerging Microbes and Infections, 2(9), e56, 9 pages, 2013.
Int'l Search Report and Written Opinion dated May 22, 2018 in Int'l Application No. PCT/IB2017/058142, 17 pages.
Obeng-Adjei et al. "DNA vaccine cocktail expressing genotype A and C HBV surface and consensus core antigens generates robust cytotoxic and antibody responses and mice and Rhesus macaques" Cancer Gene Therapy, 20, 352-662, 2013.
Cohen et al. "Is chronic hepatitis B being undertreated in the United States?" J. Viral Hepat., 18(6), 377-83,2011.
Belloni et al. "IFN-a inhibits HBV transcription and replication in cell culture and in humanized mice by targeting the epigenetic regulation of the nuclear cccDNA minichromosome" J. Clin. Invest., 122(2), 529-537, 2012.
World Health Organization, Hepatitis B: Fact sheet No. 204 [Internet] Mar. 2015. Available from https://www.who.int/news-room/fact-sheets/detail/hepatitis-b, 6 pages.
Michel et al. "Therapeutic vaccines and immune-based therapies for the treatment of chronic hepatitis B: perspectives and challenges." J. Hepatol., 54(6), 1286-1296, 2011.

Int'l Search Report and Written Opinion dated Apr. 17, 2019 in Int'l Application No. PCT/IB2018/060259, 16 pages.
Int'l Search Report and Written Opinion dated Jun. 25, 2018 in Int'l Application No. PCT/US2017/067269, 17 pages.
Int'l Search Report and Written Opinion dated Feb. 14, 2019 in Int'l Application No. PCT/US2018/066157, 19 pages.
Reyes-Sandoval Arturo et al, "Prime-Boost Immunization with Adenoviral and Modified Vaccinia Virus Ankara Vectors Enhances the Durability and Polyfunctionality of Protective Malaria CD8(+) T-Cell Responses", Infection and Immunity, (Jan. 2010), vol. 78, No. 1, pp. 145-153, XP002778539.
Perrine Martin et al, "TG1050, an immunotherapeutic to treat chronic hepatitis B, induces robust T cells and exerts an antiviral effect in HBV-persistent mice", GUT, UK, (Nov. 26, 2014), vol. 64, No. 12, doi:10.1136/gutjnl-2014-308041, ISSN 0017-5749, pp. 1961-1971, XP055453477.
Bartenschlager et al., "Expression of the P-protein of the human hepatitis B virus in a vaccinia virus system and detection of the nucleocapsid-associated P-gene product by radiolabelling at newly introduced phosphorylation sites", Nucleic Acids Research, vol. 20, No. 2, pp. 195-202,1992.
Ramirez et at., "Biology of Attenuated Modified Vaccinia Virus Ankara Recombinant Vector in Mice: Virus Fate and Activation of B- and T- Cell Immune Responses in Comparision with the Western Reserve Strain and advantages as a Vaccine", Journal of Virology, Vo. 74, No. 2, pp. 923-933, 2000.
Int'l Search Report and Written Opinion dated Mar. 26, 2018 in Int'l Application No. PCT/IB2017058148, 14 pages.
Int'l Search Report and Written Opinion dated Mar. 27, 2019 in Int'l Application No. PCT/IB2018/060257, 15 pages.
Agapov et al., Noncytopathic Sindbis Virus RNA Vectors for Heterologous Gene Expression, Proc. Natl. Acad. Sci., 1998, pp. 12989-12994, vol. 95.
Altmann et al., Cotransfection of ICAM-1 and HLA-DR Reconstitutes Human Antigen-Presenting Cell Function in Mouse L Cells, Nature, 1989, pp. 512-514, vol. 338.
Altschul SF et al., "Basic Local Alignment Search Tool"; J. Mol. Biol. 215:403-410 (1990).
Atkins, G, et al. Therapeutic and Prophylactic Applications of Alphavirus Vectors, Expert Reviews in Molecular Medicine, Cambridge University Press, vol. 10, No. 1, pp. 1-18 (2008).
Attwood, T. The Babel of Bioinformatics, Science (2000) vol. 290, No. 5491, pp. 471-473 (Year: 2000).
Barbieri et al., Purification and partial characterization of another form of the antiviral protein from the seeds of Phytolacca americana L. (pokeweed), Biochem. J., 1982, pp. 55-59, vol. 203.
Barrette-Ng et al., Structure of Arterivirus nsp-4, J. Biol. Chem., 2002, pp. 39960-39966, vol. 277, Issue 42.
Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.
Berglund, P. et al., Enhancing Immune Response Using Suicidal DNA Vaccines,, Nature Biotechnology, vol. 16, pp. 562-565 (1998).
Besnard et al., Selection against expression of the Escherichia coli gene gpt in hprt+ mouse teratocarcinoma and hybrid cells, Mol. Cell. Biol., 1987, pp. 4139-4141, vol. 7.
Brakenhoff et al., Molecular cloning and expression of hybridoma growth factor in Escherichia coli, J. Immunol., Dec. 15, 1987, pp. 4116-4121, vol. 139, Issue 12.
Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.
Calderwood et al., Nucleotide sequence of the Shiga-like toxin genes of Escherichia coli, Proc. Natl. Acad. Sci. USA, Jul. 1987, pp. 4364-4368, vol. 84.
Carroll and Collier, Active Site of Pseudomonas aeruginosa Exotoxin A, J. Biol. Chem., 1987, pp. 8707-8711, vol. 262.
Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.

(56) References Cited

OTHER PUBLICATIONS

Chen et al., The complete primary structure of abrin-a B chain. FEBS Letters, 1992, pp. 115-118, vol. 309.
Cheng, W. et al. Enhancement of Sindbis Virus Self-Replicating RNA Vaccine Potency by Linkage of Mycobacterium tuberculosis Heat Shock Protein 70 Gene to an Antigen Gene, Journal of Immunology, vol. 166, pp. 6218-6226 (2001).
Chin et al., Tissue-specific Expression of Hepatic Functions Genetic Aspects, Ann. N.Y. Acad. Sci., Oct. 1986, pp. 120-130, vol. 478.
Collins et al., Primary Amino Acid Sequence of α-Trichosanthin and Molecular Models for Abrin A-chain and α-Trichosanthin, J. Biol. Chem., 1990, pp. 8665-8669, vol. 265.
Coussens et al., Tyrosine kinase receptor with extensive homology to EGF receptor shares chromosomal location with neu oncogene, Science, 1985, pp. 1132-1139, vol. 230.
Davis, N. et al., In Vitro Synthesis of Infectious Venezuelan Equine Encephalitis Virus RNA from a cDNA Clone: Analysis of a Viable Deletion Mutant' Virology, vol. 171, pp. 189-204 (1989).
De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.
De Vries et al., Recombinant Equine Arteritis Virus Expression Vector, Virology, Jun. 5, 2001, pp. 259-276, vol. 284, Issue 2.
De Wilde et al., Cyclophilin Inhibitors Block Arterivirus Replication by Interfering with Viral RNA Synthesis, J. Virol., 2013, pp. 1454-1464, vol. 87, Issue 3.
Den Boon et al., Equine Arteritis Virus Subgenomic RNA Transcription: UV Inactivation and Translation Inhibition Studies, Virology, 1995, pp. 364-372, vol. 213.
Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.
Ding et al., In Vivo Genome-Wide Profiling of RNA Secondary Structure Reveals Novel Regulatory Features, Nature, 2014, pp. 696-700 (and Methods), vol. 505.
Dowdy et al., Efficient Generation of Human iPSCs by a Synthetic Self-Replicative RNA, Cell Stem Cell, 2013, pp. 246-254, vol. 13.
Dubensky, T. et al. Sindbis Virus DNA-Based Expression Vectors: Utility for In Vitro and In Vivo Gene Transfer, Journal of Virology, vol. 70, No. 1, pp. 508-519 (1996).
Evensen et al., Direct Molecular Cloning and Expression of Two Distinct Abrin A-chains, J. Biol. Chem., Apr. 15, 1991, pp. 6848-6852, vol. 266, Issue 11.
Fainstein et al., Nucleotide sequence analysis of human abl and bcr-abl cDNAs, Oncogene, Dec. 1, 1989, pp. 1477-1481, vol. 4. Issue 12.
Faktor et al., The identification of hepatitis B virus X gene responsive elements reveals functional similarity of X and HTLV-I tax, Oncogene, Jun. 1, 1990, pp. 867-872, vol. 5, Issue 6.
Familletti et al., A convenient and rapid cytopathic effect inhibition assay for interferon, Methods in Enz., 1981, pp. 387-394, vol. 78.
Fang et al., Efficient-2 Frameshifting by Mammalian Ribosomes to Synthesize an Additional Arterivirus Protein, PNAS, 2012, pp. E2920-E2928.
Field et al., Isolation and Characterization of Acyclovir-Resistant Mutants of Herpes Simplex Virus, J. Genl. Virol., 1980, pp. 115-124, vol. 49.
Finter et al., The Use of Interferon-α in Virus Infections, Drugs, 1991, pp. 749-765, vol. 42.
Firth et al., Discovery of a Small Arterivirus Gene that Overlaps the GP5 Coding Sequence and is Important for Virus Production, J. Genl. Virol., 2011, pp. 1097-1106, vol. 92.
Frolov, I. et al. Cis-acting RNA elements at the 5' end of Sindbis virus genome RNA regulate minus- and plus-strand RNA synthesis, RNO, vol. 7, pp. 1638-1651 (2001).

Frolov, I et al., Translation of Sindbis Virus mRNA: analysis of sequences downstream of the initiating AUG codon that enhance translation. Journal of Virology, vol. 70, No. 2, pp. 1182-1190 (1996).
Frolov, I et al.Translation of Sindbis Virus mRNA: Effects of Sequences Downstream of the Initiating Codon, Journal of Virology, vol. 68, No. 12, pp. 8111-8117, (1994).
Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.
Gibson et al., Enzymatic assembly of DNA molecules up to several hundred kilobases, Nature Methods, Apr. 12, 2009, pp. 343-345, vol. 6.
Maruggi Giulietta et al, "Engineered alphavirus replicon vaccines based on known attenuated viral mutants show limited effects on immunogenicity", Virology, (Oct. 5, 2013), vol. 447, No. 1, doi:10.1016/J.VIROL.2013.07.021, ISSN 0042-6822, pp. 254-264, XP028754361.
Glaser AL et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Gorchakov, R. et al., Selection of Functional 5 cis-Acting Elements Promoting Efficient Sindbis Virus Genome Replication, Journal of Virology, vol. 78, No. 1, pp. 61-75 (2004).
Grabstein et al., Cloning of a T cell growth factor that interacts with the beta chain of the interleukin-2 receptor. Science, 1994, pp. 965-968, vol. 264.
Hardy, R. et al Requirements at the 3 End of the Sindbis Virus Genome for Efficient Synthesis of Minus-Strand RNA, Journal of Virology, pp. 4630-4639 (2005).
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.
Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Hyde, J. et al., The 5' and 3' ends of alphavirus RNAs—non-coding is not non-functional, Virus Res., vol. 206, pp. 99-107 (2015).
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Irvin JD, Pokeweed antiviral protein, Pharmac. Ther., 1983, pp. 371-387, vol. 21, Issue 3.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Kamrud et al., Alphavirus Replicon Approach to Promoterless Analysis IRES Elements, Virology, 2007, pp. 376-387, vol. 360.
Karlin & Altschul, Applications and statistics for multiple high-scoring segments in molecular sequences Proc. Nat'l. Acad. Sci. USA 90:5873-87 (1993).
Karupiah et al., Elevated natural killer cell responses in mice infected with recombinant vaccinia virus encoding murine IL-2, J. Immunol., Jan. 1, 1990, pp. 290-298, vol. 144, Issue 1.

(56) References Cited

OTHER PUBLICATIONS

Kelly, B. et al. Potential of Alphavirus Vectors in the Treatment of Advanced Solid Tumors, Recent Patents on Anti-Drug Discovery, vol. 2, No. 2, pp. 159-166 (2007).
Kerr et al., Anti-penicillin-V-amidase conjugates kill antigen-positive tumor cells when combined with doxorubicin phenoxyacetamide, Cancer. Immunol. Immunother.,1990, pp. 202-206, vol. 31, Issue 4.
Kim et al. 2014. Enhancement of protein expression by alphavirus replicons by designing self-replicating subgenomic RNAs. Proceedings National Academy of Sciences, 111 (29):10708-10713.
Klimstra et al., Adaptation of Sindbis Virus to BHK Cells Selects for Use of Heparan Sulfate as an Attachment Receptor. J. Virol. 72: pp. 7357 (1988), 10 pages.
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).
Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.
Kofler R. et al., Mimicking live flavivirus immunization with a noninfectious RNA vaccine, PNAS, vol. 101, No. 7, pp. 1951-1956, (2004).
Kulasegaran-Shylini et al., Structural and Functional Elements of Promoter Encoded by the 5' Untranslated Region of the Venezuelan Equine Encephalitis Virus Genome J. Virol. 83:17 p. 8327-8339 (2009).
Kulasegaran-Shylini et al., The 5'UTR-specific mutation in VEEV TC-83 genome has a strong effect on RNA replication and subgenomic RNA synthesis, but not on translation of the encoded proteins. Virology, 387(1): 211-221 (2009).
Lamb et al., Nucleotide sequence of cloned cDNA coding for preproricin, Eur. J. Biochem.,1985, pp. 265-270, vol. 148.
Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.
Lehmann et al., Arterivirus nsp12 Versus the Coronavirus nsp16 2'-O-Methyltransferase: Comparison of the C-terminal Cleavage Products of Two Nidovirus pp1ab Polyproteins, J. Genl. Virol., 2015, pp. 2643-2655, vol. 96.
Lehmann et al., Arterivirus RNA-Dependent RNA Polymerase: Vital Enzymatic Activity remains Elusive, Virology, 2016, pp. 68-74, vol. 487.
Linsley et al., Binding of the B Cell activation antigen B7 to CD28 costimulates T cell proliferation and Interleukin 2 mRNA accumulation, J. Exp. Med., Mar. 1991, pp. 721-730, vol. 173.
Linsley et al., CTLA-4 Is a second receptor for the B Cell activation antigen B7, J. Exp. Med., Sep. 1991, pp. 561-570, vol. 174.
Luo, R., et al., Antiviral activity of type I and type III interferons against porcine reproductive and respiratory syndrome virus (PRRSV), Antiviral Research, vol. 91, pp. 99-101 (2011).
Maher and Dolinick, Specific hybridization arrest of dihydrofolate reductase mRNA in vitro using antisense RNA or anti-sense oligonucleotides, Arch. Biochem & Biophys., Feb. 15, 1987, pp. 214-220, vol. 253, Issue 1.
Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.
Manolaridis, et al., Structure and Genetic Analysis of the Arterivirus Nonstructural Protein 7α, J. Virol., 2011, pp. 7449-7453, vol. 85, Issue 14.
McKnight et al., Deduced consensus sequence of Sindbis virus strain AR339: mutations contained in laboratory strains which affect cell culture and in vivo phenotypes. Virol. 70:1981 (1996), 9 pages.
McLoughlin, M. et al. Alphavirus infections in salmonids—a review, Journal of Fish Diseases, vol. 30, pp. 511-531 (2007).
Mekalanos et al., Cholera toxin genes: nucleotide sequence, deletion analysis and vaccine development, Nature, 1983, pp. 551-557, vol. 306.
Mogler, M. et al., RNA-based viral vectors, Expert Rev. Vaccines, pp. 1-30 (2014).
Molenkamp R et al, "The arterivirus replicase is the only viral protein required for genome replication and subgenomic mRNA transcription.", The Journal of General Virology Oct. 2000, (Oct. 2000), vol. 81, No. Pt 10, ISSN 0022-1317, pp. 2491-2496, XP002771366.
Molenkamp et al., Isolation and Characterization of an Arterivirus Defective Interfering RNA Genome, J. Virol., 2000, pp. 3156-3165, vol. 74, Issue 7.
Molenkamp et al., Characterization of an Arterivirus Defective Interfering RNA, 2001, pp. 519-525. In the Nidoviruses (Coronaviruses and Arteriviruses), Ehud Lavi et al. (ed.), Kluwer Academic/Plenum Publishers.
Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.
Muraggi, G et al. Engineered Alphavirus Replicon Vaccines Based on Known Attenuated Viral Mutants Show Limited Effects on Immunogenicity, Virology, vol. 44, pp. 254-264 (2013).
Nagata, et al., Synthesis in E. coli of a polypeptide with human leukocyte interferon activity, Nature, 1980, pp. 316-320, vol. 284.
Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.
Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.
Needleman, S. et al., A general method applicable to the search for similarities in the amino acid sequence of two proteins J. Mol. Biol. 48:443-53 (1970).
Nolz, J et al. Strategies and Implications for Prime-Boost Vaccination to Generate Memory CD8 T Cells, Advances in Experimental Medicine and Biology, pp. 69-83, (2011).
Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.
Pasternak, Sequence requirements for RNA strand transfer during nidovirus discontinuous subgenomic RNA synthesis, EMBO J., 2001, pp. 7220-7228, vol. 20, Issue 24.
Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.
Pasternak, Regulation of Relative Abundance of Arterivirus Subgenomic mRNAs, J. Viral., Aug. 2004, pp. 8102-8113, vol. 78, Issue 15.
Pearson, W. et al., Improved tools for biological sequence comparison, Proc. Natl. Acad. Sci. US, vol. 85, pp. 2444-2448 (1988).
Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.
Perri et al., Replicon Vectors Derived from Sindbis Virus and Semliki Forest Virus that Establish Persistent Replication in Host Cells, J. Virol., 2000, pp. 9802-9807, vol. 74, Issue 20.
Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145 (2006).
Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.

(56) References Cited

OTHER PUBLICATIONS

Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.

Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.

Pushko et al., Replicon-Helper Systems from Attenuated Venezuelan Equine Encephalitis Virus: Expression of Heterologous Genes In Vitro and Immunization against Heterologous Pathogens In Vivo, Virology, Dec. 22, 1997, pp. 389-401, vol. 239, Issue 2.

Radford et al., Cell-Type Specificity of Interferon-γ-Mediated HLA Class I Gene Transcription in Human Hematopoietic Tumor Cells. American Society of Hepatology, 1991, pp. 2008-2015.

Rice, C. et al., Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants, Journal of Virology, vol. 61, No. 12, pp. 3809-3819 (1987).

Rogne et al., The isolation and characterisation of a cDNA clone for human lecithin:cholesterol acyl transferase and its use to analyze the genes in patients with LCAT deficiency and fish eye disease, Biochem, Biophys. Res. Commun., 1987, pp. 161-169, vol. 148, Issue 1.

Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.

Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.

Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.

Shylini, R Structure-Function Studies of the Venezuelanequine Encephalitis Virus 5'utr Promoter Element and Its Role in Attenuation of the Virus, Dissertation for Doctor of Philosophy, The University of Texas Medical Branch (2009) 147 pages.

Sjoberg,E et al., A Significantly Improved Semliki Forest Virus Expression System Based on Translation Enhancer Segments from the Viral Capsid Gene, Biotechnology, Vo,. 12, pp. 1127-1131, (1994).

Smith et al., Comparison of Biosequences, Adv. Appl. Math., 2:482-89 (1981).

Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.

Snijder, E.J., Arterivirus RNA Synthesis Dissected, 2001, pp. 241-253. In the Nidoviruses (Coronaviruses and Arteriviruses), Ehud Lavi et al. (ed.), Kluwer Academic/Plenum Publishers.

Snijder et al., Proteolytic Processing of the Arterivirus Replicase, 1995, pp. 443-451. In Corona—and Related Viruses, P.J. Talbot and G.A. Levy (ed.), Plenum Press, NY.

Snijder et al., The Arterivirus Nsp2 Protease, J. Biol. Chem., 1995, pp. 16671-16676, vol. 270, Issue 28.

Snijder et al., Heterodimerization of the Two Major Envelope Proteins is Essential for Arterivirus Infectivity, J. Viral., 2003, pp. 97-104, vol. 77, Issue 1.

Snijder et al., 2005. The order Nidovirales, pp. 390-404, In Topley and Wilson's microbiology and microbial infections, B. W. Mahy and V. ter Meulen (ed.), Hodder Arnold, London, United Kingdom.

Snijder EJ et al., "Identification of a Novel Structural Protein of Arteriviruses," J. Virol, Aug. 1999, pp. 6335-6345, vol. 37, Issue 8.

Stanton et al., Nucleotide sequence comparison of normal and translocated murine c-myc genes, Nature, Aug. 1984, pp. 423-425, vol. 310.

Strauss etal., The AlpahViruses: Gene Expression, Replication and Evolution, Microbiological Reviews, pp. 491-562, Sep. 1994.

Stirpe et al., Gelonin, a New Inhibitor of Protein Synthesis, Non-toxic to Intact Cells, J. Biol. Chem., Jul. 25, 1980, pp. 6947-6953, vol. 255.

Te Velthuis, et al., Zn2+ Inhibits Coronavirus and Arterivirus RNA Polymerase Activity In Vitro and Zinc Ionophores Block the Replication of these Viruses in Cell Culture, PLoS Pathogens, 2010, e1001176, pp. 1-10, vol. 6, Issue 11.

Tepper et al., Murine interleukin-4 displays potent anti-tumor activity in vivo, Cell, May 5, 1989, pp. 503-512, vol. 57.

Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.

Tijerina et al., DMS Footprinting of Structured RNAs and RNA-Protein Complexes, Nat. Protoc., 2007, pp. 2608-2623, vol. 2, Issue 10.

Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.

Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.

Toribio et al., Inhibition of host translation by virus infection in vivo, PNAS, vol. 107, No. 21, pp. 9837-9842 (2010).

Toribio et al., An RNA Trapping Mechanism in Alphavirus MRNA Promotes Translation and Initiation Nucleic Acids Res. 19, 44(9): pp. 4368-4380 (2016).

Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.

Twu et al., Hepatitis B virus X gene can transactivate heterologous viral sequences, Proc Natl. Acad. Sci. USA, Mar. 1989, pp. 2046-2050, vol. 86.

Van Aken et al., Expression, Purification, and In Vitro Activity of an Arterivirus Main Proteinase, Virus Res., 2006, pp. 97-106, vol. 120.

Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.

Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.

Van Den Born, Value of routine funduscopy in patients with hypertension: systematic review, BMJ, Jul. 9, 2005, pp. 1-5, vol. 331.

Van Den Born, et al., "An infectious recombinant equine arteritis virus expressing green fluorescent protein from its replicase gene," J. Genl. Virol., Apr. 2007, pp. 1196-1205, vol. 88.

Van Der Meer et al., ORF1a-Encoded Replicase Subunits are Involved in the Membrane Association of the Arterivirus Replication Complex, J. Virol., 1998, pp. 6689-6698, vol. 72, Issue 8.

Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.

Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 3, Issue 3.

Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.

Van Hemert et al., The In Vitro RNA Synthesizing Activity of the Isolated Arterivirus Replication/Transcription Complex is Dependent on a Host Factor, J. Biol. Chem., 2008, pp. 16525-16536, vol. 283, Issue 24.

(56) References Cited

OTHER PUBLICATIONS

Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.

Van Kasteren et al., Deubiquitinase Function of Arterivirus Papain-Like Protease 2 Suppresses the Innate Immune Response in Infected Host Cells, PNAS, 2013, pp. E838-E847.

Van Marle, et al., Characterization of an Equine Arteritis Virus Replicase Mutant Defective in Subgenomic mRNA Synthesis, J. Virol., 1999, pp. 5274-5281, vol. 73, Issue 7.

Van Marle et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.

Ventoso, I., Adaptive Changes in Alphavirus mRNA Translation Allowed Colonization of Vertebrate Hosts, Journal of Virology, vol. 86, No. 17, pp. 9484-9494 (2012).

Ventoso, I. et al. Translational resistance of late alphavirus mRNA to eIF2 phosphorylation: a strategy to overcome the antiviral effect of protein kinase PKR, Genes and Development, vol. 20, pp. 87-100 (2006).

Vrudhula et al., Prodrugs of doxorubicin and melphalan and their activation by a monoclonal antibody-penicillin-G amidase conjugate, J. Med. Chem., 1993, pp. 919-923, vol. 36, Issue 7.

Ward, S. et al., Generation of CTL responses using Kunjin replicon RNA, Immunology and Cell Biology, vol. 81, pp. 73-78 (2003).

Warner et al. Induction of the HIV-Specific and Antibody Responses in Mice Using Retroviral Vector-Transduced Cells, AIDS Res. and Human Retroviruses, vol. 7, No. 8, pp. 645-655 (1991).

Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.

Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.

Weber et al., Immunotherapy of a murine tumor with interleukin 2. J. Exp. Med., 1987, pp. 1716-1733, vol. 166.

White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718 (2001).

Wilson et al., Prospects for gene therapy of familial hypercholesterolemia, Mol. Biol. Med., Jun. 1, 1990, pp. 223-232, vol. 7, Issue 3.

Wood et al., Preproabrin: genomic cloning, characterisation and the expression of the A-chain in *Escherichia coli*, Eur. J. Biochem., 1991, pp. 723-732, vol. 198.

Yamamoto et al., The human LDL receptor: a cysteine-rich protein with multiple Alu sequences in its mRNA, Cell, Nov. 1984, pp. 27-38, vol. 39, Issue 1.

Zhou, X. et al. Self-replicating Semliki Forest virus RNA as recombinant vaccine, Vaccine, vol. 12, No. 16, pp. 1510-1514 (1994).

GenBank/NCBI accession No. J02363, dated Oct. 25, 2000; accessed Jul. 16, 2018, 7 pages.

GenBank accession # JX473847, dated Dec. 22, 2012; accessed Apr. 17, 2019, 6 pages.

GenBank/NCBI accession No. L01443.1., dated Nov. 17, 2014; accessed Oct. 3, 2016, 7 pages.

GenBank/NCBI accession No. L04653, dated Jun. 1, 2001; accessed Jul. 16, 2018, 6 pages.

GenBank/NCBI accession No. NC_001449, dated Feb. 10, 2015; accessed Jul. 16, 2018, 7 pages.

GenBank/NCBI accession No. NC_003215, dated Feb. 10, 2015; accessed Jul. 16, 2018, 6 pages.

GenBank/NCBI accession No. U38304; dated Feb. 10, 2015; accessed Jul. 16, 2018, 5 pages.

GenBank/NCBI accession No. U38305, dated Jan. 30, 2016, accessed Jul. 16, 2018, 5 pages.

GenBank/NCBI accession No. X04129, dated Mar. 13, 2001; accessed Jul. 16, 2018, 5 pages.

International Search Report and Written Opinion, dated Dec. 1, 2017, in International Application No. PCT/US2017/054928, 18 pages.

International Search Report and Written Opinion, dated Jul. 10, 2017, in International Patent Application No. PCT/US2017/027249, filed Apr. 12, 2017, 16 pages.

International Search Report and Written Opinion, dated Jul. 3, 2018, in International Application No. PCT/US2017/064561, 22 pages.

Kim, et al., "New World and Old World Alphaviruses Have Evolved to Exploit Different Components of Stress Granules, FXR and G3BP Proteins, for Assembly of Viral Replication Complexes", PLOS Pathogens, vol. 12, No. 8, p. 1-31, (Aug. 2016).

Foy, et al., "Hypervariable domains of nsP3 proteins of New World and Old World alphaviruses mediate formation of distinct, virus-specific protein complexes", J. Virol., vol. 87, No. 4, p. 1997-2010, (Dec. 2012).

Gotte, et al., "The Enigmatic Alphavirus Non-Structural Protein 3 (nsP3) Revealing Its Secrets at Last", Viruses, vol. 10, No. 3, p. 105, 1/26 to 26/26, (Feb. 2018).

Meshram, et al., "Multiple Host Factors Interact with the Hypervariable Domain of Chikungunya Virus nsP3 and Determine Viral Replication in Cell-Specific Mode", J. Virol., vol. 92, No. 16, p. 1-24, (Aug. 2018).

International Search Report and Written Opinion dated Dec. 13, 2019 in International Appl. No. PCT/US2019/055125, 15 pages.

Tian et al. Arterivirus minor envelope proteins are a major determinant of viral tropism in cell culture. J Virol. Apr. 2012;86(7):3701-12. (Year: 2012).

Baker et al., Protein Structure Predication and Structural Genomics, Science (2001) vol. 294, No. 5540, pp. 93-96 (Year: 2001).

Huang et al. Development of a vaccine vector based on a subgenomic replicon of porcine reproductive and respiratory syndrome virus. J Virol Methods. Sep. 2009;160(1-2):22-8. (Year: 2009).

Yin et. al. Similarities and Differences in Antagonism of Neuron Alpha/Beta and Sindbis Alphaviruses 2009. Journal of Virology. 83 ( 19) p. 10036-10047 (Year: 2009).

Mir et. al. A Multicistronic DNA Vaccine Induces Significant Protection against Tuberculosis in Mice and Offers Flexibility in the Expressed Antigen Repertoire. 2009. Clinical and Vaccine Immunology. vol. 16, No. 10. p. 1467-1475 (Year: 2009).

* cited by examiner

```
                            SEQUENCE LISTING

<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: conserved T cell epitope

<400> SEQUENCE: 1

Ile Tyr Ser Thr Val Ala Ser Ser Leu
1               5

<210> SEQ ID NO 2
<211> LENGTH: 145
<212> TYPE: DNA
<213> ORGANISM: Sindbis virus

<400> SEQUENCE: 2
atagtcagca tagtacattt catctgacta atactacaac accaccacca tgaatagagg      60
attctttaac atgctcggcc gccgcccctt cccggccccc actgccatgt ggaggccgcg     120
gagaaggagg caggcggccc cgatg                                           145

<210> SEQ ID NO 3
<211> LENGTH: 104
<212> TYPE: DNA
<213> ORGANISM: Sindbis virus

<400> SEQUENCE: 3
atgaatagag gattctttaa catgctcggc cgccgcccct cccggcccc cactgccatg       60 tggaggccgc ggagaaggag gcaggcggcc ccgatgcctg cccg                      104

<210> SEQ ID NO 4
<211> LENGTH: 120
<212> TYPE: DNA
<213> ORGANISM: Aura virus

<400> SEQUENCE: 4
atgaactctg tcttttacaa tccgtttggc cgaggtgcct acgctcaacc tccaatagca      60
tggaggccaa gacgtagggc tgcacctgcg cctcgaccat ccgggttgac tacccagatc     120

<210> SEQ ID NO 5
<211> LENGTH: 71
<212> TYPE: DNA
<213> ORGANISM: Eastern Equine Encephalitis virus SA

<400> SEQUENCE: 5
atgtttccgt atccaacatt gaactacccg cctatggcac cggttaatcc gatggcatac      60
agggacccca a                                                           71

<210> SEQ ID NO 6
<211> LENGTH: 91
<212> TYPE: DNA
<213> ORGANISM: O'Nyong-Nyong virus

<400> SEQUENCE: 6
atggagttca taccagcaca aacttactac aatagaagat accagcctag accctggact      60
```

```
caacgccta ctatccaggt gatcaggcca a                                        91

<210> SEQ ID NO 7
<211> LENGTH: 67
<212> TYPE: DNA
<213> ORGANISM: Semliki Forest virus

<400> SEQUENCE: 7
atgaattaca tccctacgca aacgttttac ggccgccggt ggcgcccgcg cccggcggcc        60
cgtcctt                                                                 67

<210> SEQ ID NO 8
<211> LENGTH: 69
<212> TYPE: DNA
<213> ORGANISM: Ross River virus

<400> SEQUENCE: 8
atgaattaca taccaaccca gacttttac ggacgccgtt ggcggcctcg cccggcgttc         60
cgtccatgg                                                               69

<210> SEQ ID NO 9
<211> LENGTH: 91
<212> TYPE: DNA
<213> ORGANISM: Mayaro virus

<400> SEQUENCE: 9
atggatttcc taccaacaca agtgttttat ggcaggcgat ggagaccacg aatgccgcca        60
cgcccttgga ggccacgccc acctacaatt c                                      91
```

INDUCE AND ENHANCE IMMUNE RESPONSES USING RECOMBINANT REPLICON SYSTEMS

CROSS-REFERENCE TO RELATED APPLICATIONS

This application claims benefit of priority under 35 U.S.C. § 119(e) of U.S. Ser. No. 62/619,540, filed Jan. 19, 2018, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2230_1WO_Sequence_Listing.txt, was created on Jan. 16, 2019, and is 3 kb. The file can be accessed using Microsoft Word on a computer that uses Windows OS.

FIELD

Aspects of the present disclosure relate to the field of virology, infectious diseases, and immunology. More particularly, the disclosure relates to compositions and methods for inducing and/or enhancing an immune response in a subject by the sequential administration of at least two immunogenic compositions comprising different RNA replicons.

BACKGROUND

Generating a large population of antigen-specific memory CD8 T cells is a desirable goal for vaccine design against a variety of animal and human diseases. Numerous studies performed on experimental models have demonstrated that the overall number of antigen-specific memory CD8 T cells present at the time of infection correlates strongly with the ability to confer host protection against a range of different pathogens. Currently, one the most conceivable approaches to rapidly generate a large population of memory CD8 T cells is through the use of prime-boost vaccination. Indeed, multi-dose immunizations, for therapy or for disease prevention, have been reported to be often more effective than single-dose immunizations. This difference has been observed for different types of vaccines, including live attenuated vaccines, inactivated vaccines, recombinant protein subunit vaccines, and polysaccharide vaccines. There is still a need for more effective heterologous prime-boost regimes.

SUMMARY

This section provides a general summary of the present application and is not comprehensive of its full scope or all of its features.

The present disclosure provides compositions and methods for delivering two RNA replicons into a subject for various applications. In some embodiments, the compositions and methods disclosed herein allow for inducing and/or enhancing an immune response in the subject. In some embodiments, the compositions and methods disclosed herein can be used for the production of a molecule of interest, such as, for example, a therapeutic polypeptide in the subject.

In one aspect, some embodiments disclosed herein relate to a method for inducing an immune response in a subject, the method includes administering to the subject at least one dose of a priming composition comprising a first RNA replicon which encodes a first antigen; and subsequently administering to the subject at least one dose of a boosting composition comprising a second RNA replicon which encodes a second antigen, wherein the first and second RNA replicons are different from each other. The first and second RNA replicons can be any described herein.

In another aspect, some embodiments disclosed herein relate to a method for delivering two RNA replicons into a subject, the method includes administering to the subject a first nucleic acid sequence encoding a first RNA replicon which encodes a first antigen; and subsequently administering to the subject a second nucleic acid sequence encoding a second RNA replicon which encodes a second antigen, wherein the first and second RNA replicons are different from each other. The first and second RNA replicons can be any described herein.

Implementations of embodiments of the methods according to the present disclosure can include one or more of the following features. In some embodiments, the first antigen and the second antigen are identical to each other. In some embodiments, amino acid sequences of the first and the second antigens are homologous to each other. In some embodiments, the amino acid sequence of the first antigen exhibits at least 80%, 85%, 90%, 95%, 96%, 97%, 98%, or 99% sequence identity to the amino acid sequence of the second antigen. In some embodiments, the first and the second antigens comprise at least one cross-reactive antigenic determinant. In some embodiments, the first and the second antigens induce substantially the same immune response in the subject. In some embodiments, the first RNA replicon is capable of activating an immune system of the subject through at least one immunological mechanism that is different from an immunological mechanism by which the immune system is capable of being activated by the second RNA replicon. In some embodiments, the at least one immunological mechanism is selected from the group consisting of differential activation of protein kinase R (PKR), retinoic acid-inducible gene I (RIG-I), autophagy pathways, Toll-like receptors (TLRs), stress granules, RNase R, and oligoadenylate synthetases (OAS).

In some embodiments disclosed herein, at least one of the first and second RNA replicons is a modified RNA replicon. In some embodiments, at least one of the first and second RNA replicons is derived from a positive-strand RNA virus. In some embodiments, at least one of the first and second RNA replicons is derived from a virus species belonging to a family selected from the group consisting of Togaviridae family, Flaviviridae family, Orthomyxoviridae family, Rhabdoviridae family, Arteroviridae family, Picornaviridae family, Astroviridae family, Coronaviridae family, and Paramyxoviridae family. In some embodiments, at least one of the first and second RNA replicons is derived from an Alphavirus or an Arterivirus. In some embodiments, at least one of the first and second RNA replicons is derived from an alphavirus species selected from the group consisting of Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu virus (NDUV), Salmonid alphavirus (SAV), and Buggy Creek virus (BCRV).

In some embodiments disclosed herein, both of the first and second RNA replicons are derived from alphavirus species. In some embodiments, the first and second RNA replicons are derived from the same alphavirus species or from two different alphavirus species. In some embodiments, the first RNA replicon is derived from an alphavirus and the second RNA replicon is derived from a non-alphavirus species. In other embodiments the first RNA replicon is derived from a non-alphavirus and the second RNA replicon is derived from an alphavirus species. In some embodiments the first RNA replicon is derived from an Arterivirus (e.g. EAV) and the second RNA replicon is derived from an alphavirus (e.g. VEEV). In some embodiments, at least one of the first and second RNA replicons comprises a modified 5'-UTR with one or more nucleotide substitutions at position 1, 2, 4, or a combination thereof. In some embodiments, at least one of the one or more nucleotide substitutions is a nucleotide substitution at position 2 of the modified 5'-UTR. In some embodiments, the nucleotide substitution at position 2 of the modified 5'-UTR is a U→G substitution.

In some embodiments, at least one of the first and second RNA replicons is a modified RNA replicon comprising a modified 5'-UTR and is devoid of at least a portion of a nucleic acid sequence encoding one or more viral structural proteins. In some embodiments, the modified RNA replicon is devoid of a substantial portion of the nucleic acid sequence encoding one or more viral structural proteins. In some embodiments, the modified RNA replicon comprises no nucleic acid sequence encoding viral structural proteins. In some embodiments, at least one of the first and second RNA replicons is a modified alphavirus replicon comprising one or more RNA stem-loops in a structural element of a viral capsid enhancer. In some embodiments, at least one of the first and second RNA replicons is a modified alphavirus replicon comprising coding sequence for a heterologous non-structural protein nsP3. In some embodiments, the heterologous non-structural protein nsP3 is a Chikungunya virus (CHIKV) nsP3 or a Sindbis virus (SINV) nsP3. In some embodiments, at least one of the first and second antigens is expressed under control of a 26S subgenomic promoter or a variant thereof. In some embodiments, the 26S subgenomic promoter is a SINV 26S subgenomic promoter, RRV 26S subgenomic promoter, or a variant thereof.

In some embodiments disclosed herein, at least one of the first and second RNA replicons is derived from an arterivirus species selected from the group consisting of Equine arteritis virus (EAV), Porcine respiratory and reproductive syndrome virus (PRRSV), Lactate dehydrogenase elevating virus (LDV), and Simian hemorrhagic fever virus (SHFV). In some embodiments, both of the first and second RNA replicons are derived from arterivirus species. In some embodiments, the first and second RNA replicons are derived from the same arterivirus species or from two different arterivirus species. In some embodiments, the first RNA replicon is derived from an arterivirus, and the second RNA replicon is derived from a non-arterivirus species. In some embodiments, the first RNA replicon is derived from an arterivirus and the second RNA replicon is derived from an alphavirus. In some embodiments, the first RNA replicon is an unmodified RNA replicon derived from an arterivirus species. In some embodiments, the first RNA replicon is a modified RNA replicon derived from an arterivirus species. In some embodiments, the first RNA replicon is an RNA replicon derived from an alphavirus species and the second RNA replicon is an RNA replicon derived from an arterivirus species. In some embodiments, the first RNA replicon is an unmodified RNA replicon derived from an alphavirus species. In some embodiments, the first RNA replicon is a modified RNA replicon derived from an alphavirus species.

In some embodiments disclosed herein, the method according to this aspect and other aspects of the disclosure further includes one or more subsequent boosting steps, e.g., one or more subsequent administrations of the boosting composition. In some embodiments, one or more of the priming composition and the boosting composition further comprises a pharmaceutically acceptable carrier. In some embodiments, the subject is an aquatic animal. In some embodiments, the subject is an avian species, a crustacean species, or a fish species. In some embodiments, the avian species is an avian species for food consumption. In some embodiments, the crustaceans are shrimp. In some embodiments, the fish species is a fish species used in aquaculture. In some embodiments, the subject is a mammal. In some embodiments, the mammal is human, horse, pig, primate, mouse, ferret, rat, cotton rat, cattle, swine, sheep, rabbit, cat, dog, goat, donkey, hamster, or buffalo.

In one aspect, some embodiments disclosed herein relate to a composition which comprises: a priming composition comprising a first RNA replicon which encodes a first antigen; and a boosting composition comprising a second RNA replicon which encodes a second antigen, wherein the first and second RNA replicons are different from each other.

In another aspect, some embodiments disclosed herein relate to a composition which comprises: a first nucleic acid sequence encoding a first RNA replicon which encodes a first antigen; and a second nucleic acid sequence encoding a second RNA replicon which encodes a second antigen, wherein the first and second RNA replicons are different from each other, wherein the first replicon and the second replicon comprises at least one expression cassette comprising a promoter operably linked to a coding sequence for a molecule of interest. The first RNA replicon and second RNA replicon can be any described herein.

Implementations of embodiments of the compositions according to the above aspects of the present disclosure can include one or more of the following features. In some embodiments, the first and the second antigens are identical to each other. In some embodiments, amino acid sequences of the first and the second antigens are homologous to each other. In some embodiments, the amino acid sequence of the first antigen exhibits at least 80%, 85%, 90%, 95%, 96%, 97%, 98%, or 99% sequence identity to the amino acid sequence of the second antigen. In some embodiments, the first and the second antigens comprise at least one cross-reactive antigenic determinant. In some embodiments, the first and the second antigens induce substantially the same immune response in the subject. In some embodiments, the first RNA replicon can activate an immune system of the subject through at least one immunological mechanism that is different from an immunological mechanism by which the immune system can be activated by the second RNA replicon. In some embodiments, the at least one immunological mechanism is selected from the group consisting of differential activation of protein kinase R (PKR), retinoic acid-inducible gene I (RIG-I), autophagy pathways, Toll-like receptors (TLRs), stress granules, RNase R, and oligoadenylate synthetases (OAS).

In some embodiments disclosed herein, at least one of the first and second RNA replicons is a modified replicon. In some embodiments, at least one of the first and second RNA replicons is derived from a positive-strand RNA virus. In some embodiments, at least one of the first and second RNA replicons is derived from a virus species belonging to a family selected from the group consisting of Togaviridae family, Flaviviridae family, Orthomyxoviridae family, Rhabdoviridae family, Arteroviridae family, Picornaviridae family, Astroviridae family, Coronaviridae family, and Paramyxoviridae family. In some embodiments, at least one of the first and second RNA replicons is derived from an Alphavirus or an Arterivirus. In some embodiments, at least one of the first and second RNA replicons is derived from an alphavirus species selected from the group consisting of any one or more of: Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu virus (NDUV), Salmonid alphavirus (SAV), and Buggy Creek virus (BCRV), or from a group consisting of every possible combination or sub-combination of the viruses. For example in some embodiments the alphavirus species can be selected from the group consisting of Eastern equine encephalitis virus (EEEV), Venezuelan equine encephalitis virus (VEEV), and Everglades virus (EVEV).

In some embodiments disclosed herein, both of the first and second RNA replicons are derived from alphavirus species. In some embodiments, the first and second RNA replicons are derived from the same alphavirus species or from two different alphavirus species. In some embodiments, the first RNA replicon is derived from an alphavirus and the second RNA replicon is derived from a non-alphavirus species. In some embodiments, at least one of the first and second RNA replicons comprises a modified 5'-UTR with one or more nucleotide substitutions at position 1, 2, 4, or a combination thereof. In some embodiments, at least one of the one or more nucleotide substitutions is a nucleotide substitution at position 2 of the modified 5'-UTR. In some embodiments, the nucleotide substitution at position 2 of the modified 5'-UTR is a U→G substitution.

In some embodiments, at least one of the first and second RNA replicons is a modified RNA replicon comprising a modified 5'-UTR and is devoid of at least a portion of a nucleic acid sequence encoding one or more viral structural proteins. In some embodiments, the modified RNA replicon is devoid of a substantial portion of the nucleic acid sequence encoding one or more viral structural proteins. In some embodiments, the modified RNA replicon comprises no nucleic acid sequence encoding viral structural proteins. In some embodiments, at least one of the first and second RNA replicons is a modified alphavirus replicon comprising one or more RNA stem-loops in a structural element of a viral capsid enhancer or a variant thereof. In some embodiments, at least one of the first and second RNA replicons is a modified alphavirus replicon comprising a coding sequence for a heterologous non-structural protein nsP3. In some embodiments, the heterologous non-structural protein nsP3 is a Chikungunya virus (CHIKV) nsP3, a Sindbis virus (SINV) nsP3, or a variant thereof. In some embodiments, at least one of the first and second antigens is expressed under control of a 26S subgenomic promoter or a variant thereof. In some embodiments, the 26S subgenomic promoter is a SINV 26S subgenomic promoter, RRV 26S subgenomic promoter, or a variant thereof.

In some embodiments disclosed herein, at least one of the first and second RNA replicons is derived from an arterivirus species selected from the group consisting of Equine arteritis virus (EAV), Porcine respiratory and reproductive syndrome virus (PRRSV), Lactate dehydrogenase elevating virus (LDV), and Simian hemorrhagic fever virus (SHFV). In some embodiments, both of the first and second RNA replicons are derived from an arterivirus species. In some embodiments, the first and second RNA replicons are derived from the same arterivirus species or from two different arterivirus species. In some embodiments, the first RNA replicon is derived from an arterivirus, and the second RNA replicon is derived from a non-arterivirus species. In some embodiments, the first RNA replicon is derived from an arterivirus and the second RNA replicon is derived from an alphavirus. In some embodiments, the first RNA replicon is an unmodified RNA replicon derived from an arterivirus species. In some embodiments, the first RNA replicon is a modified RNA replicon derived from an arterivirus species. In some embodiments, the first RNA replicon is an RNA replicon derived from an alphavirus species and the second RNA replicon is an RNA replicon derived from an arterivirus species. In some embodiments, the first RNA replicon is an unmodified RNA replicon derived from an alphavirus species. In some embodiments, the first RNA replicon is a modified RNA replicon derived from an alphavirus species.

In some embodiments disclosed herein, the compositions according to the present disclosure further comprise compositions for one or more subsequent boosting steps, e.g., one or more subsequent administrations of the boosting composition. In some embodiments, one or more of the priming composition and the boosting composition further comprises a pharmaceutically acceptable carrier. In some embodiments, the subject is a mammal. In some embodiments, the mammal is human, horse, pig, primate, mouse, ferret, rat, cotton rat, cattle, swine, sheep, rabbit, cat, dog, goat, donkey, hamster, or buffalo.

The foregoing summary is illustrative only and is not intended to be in any way limiting. In addition to the illustrative embodiments and features described herein, further aspects, embodiments, objects and features of the application will become fully apparent from the drawings, the detailed description, and the claims.

BRIEF DESCRIPTION OF THE DRAWINGS

In FIG. 2A, mean frequencies of effector IFN-γ-secreting CD8+ T cell responses were determined by enzyme-linked immunospot (ELISpot) assays on splenocytes derived from immunized BALB/c mice 14 days after boost (a stands for alphavirus replicon). In FIG. 2B, geometric means of total IgG titers (inverse of ED20%) at 14 days after boost were determined by enzyme-linked immunosorbent assays (ELISA). All immune responses are shown with 95% confidence intervals and statistics displayed are using non-parametric unpaired Mann-Whitney test.

Figure 1:
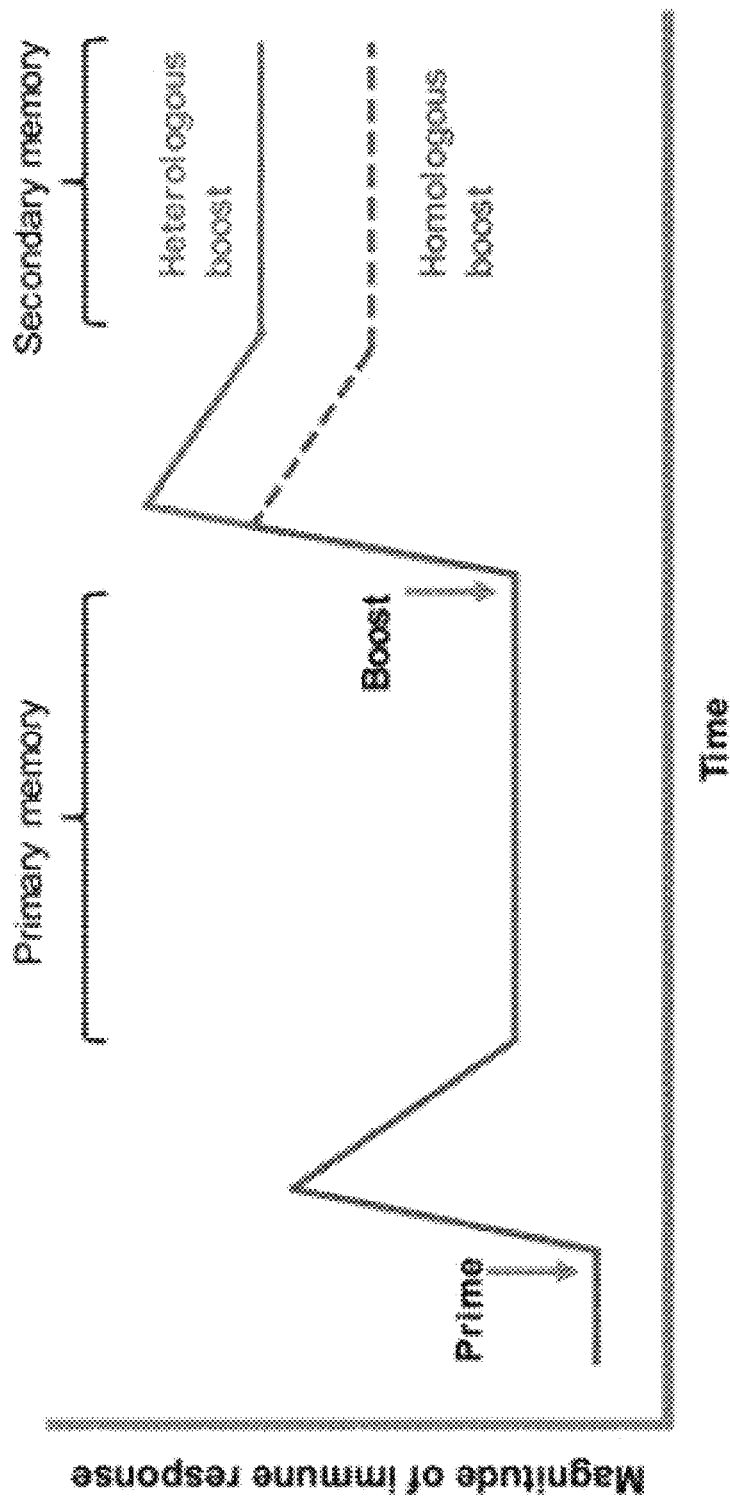
FIG. 1 is a schematic illustration of a non-limiting example of a method of inducing an immune response in a subject in accordance with some embodiments of the disclosure. In this example, the magnitude of immune response, as determined by total number of antigen specific CD8 T cells, to a traditional prime-boost regimen (dashed line) or to a heterologous prime-boost regimen (solid line) is plotted over time.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION OF THE DISCLOSURE

The present disclosure generally relates to the use of different self-amplifying mRNA molecules to enhance immune responses, for example immune responses following prophylactic vaccination and/or therapeutic administration. Some embodiments of the disclosure relate to compositions and methods for inducing an immune response in a subject using heterologous prime-boost immunization regimens that can be used prophylactically and/or therapeutically. In some embodiments, the compositions and methods disclosed herein can be deployed for the production of a molecule of interest, e.g., a therapeutic polypeptide, in a subject.

Generating a large population of antigen-specific memory CD8 T cells is a desirable goal for vaccine design against a variety of animal and human diseases. One approach to efficaciously generate a large population of memory CD8 T cells is through the use of prime-boost vaccination in a "heterologous" prime-boost format, which involves priming the generation of memory CD8 T cells with an antigen delivered in one vector and then administering the same antigen, or essentially the same antigen, in the context of a different vector at a later time point.

Some embodiments disclosed herein relate to heterologous prime-boost regimens that involve sequential administrations of the same immunogen using two different modalities as a strategy to elicit superior immune responses in subjects. This strategy can be employed for a variety of challenging pathogens including, but are not limited to, malaria, HIV, TB, and Ebola. Heterologous prime-boosts can result in superior memory responses, a higher magnitude of CD8+ T cell responses, a broadening of T cell epitopes recognized by the immune system, and an increase in polyfunctionality of T cells. Alphavirus-derived replicons (for example, Sindbis, VEE, and Semliki-forest virus) have been employed in heterologous prime-boost settings in combination with protein, DNA, and virosomes. These have proven to be effective in small animal models in mice for human papillomavirus (HPV) and human immunodeficiency virus (HIV), as well as in non-human primates (NHPs) with the replicon being delivered in the particle form for Dengue. Furthermore, fully synthetic Alphavirus-derived replicons have been used extensively in homologous prime-boost regimes. The invention provides regimens having two immunologically different replicons for use in heterologous prime-boost regimens. The invention also provides regimens having repeated administration of Alphavirus-derived replicons expressing therapeutic proteins that can employ either homologous or heterologous administration regimens.

As disclosed herein, by priming and boosting the generation of memory CD8 T cells with two immunologically different RNA replicons, immune responses can be strategically improved to tackle more complex pathogens. For example, with regards to vaccines, recall responses can be negatively impacted by pre-existing antibodies or T cell responses to the platform delivering the antigen (anti-vector immunity). Similarly, multiple administrations of the antigen using the same platform stimulates the immune system in the exact same way, but may be more inherently self-limiting due to its inability to synergize with alternate mechanisms of immune detection. Without being bound to any particular theory, it is believed that heterologous prime-boost immunization functions to circumvent the first problem since it can be designed to bypass pre-existing antibodies or T cells responses depending on the causative mechanism of reduced responses. Furthermore, heterologous prime-boosts using two immunologically different replicons can be engineered so that the follow-on administrations activate the immune system in different ways that synergize with the initial administration.

In another example, with regards to therapeutics, recall response can reduce the duration and magnitude of heterologous protein expression as immune responses directed against the vector can result in the clearance of cells expressing the therapeutic protein. Without being bound to any particular theory, it is believed that heterologous prime-boost immunization bypasses this issue by reducing the ability for the immune system to recognize the replicon that is expressing the protein upon repeat administrations, thereby delaying clearance.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and made part of this application.

Unless otherwise defined, all terms of art, notations and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

The singular form "a", "an", and "the" include plural references unless the context clearly dictates otherwise. For example, the term "a cell" includes one or more cells, comprising mixtures thereof "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The term "antigenic determinant" or "epitope", as used herein, refers to a part of an antigen (e.g., a polypeptide), for example a part of the primary, secondary, tertiary, or quaternary structure of the antigen, that is recognized by the immune system, for example antibodies, B cells (e.g., B lymphocytes) and/or T cells. In some embodiments, the antigenic determinant is a site on the surface of the antigen. In some embodiments, the antigenic determinant is a site that an antibody molecule binds to the antigen. The term "cross-reactive antigenic determinant" refers to the ability of an antigenic determinant present on two or more different antigen molecules (e.g., polypeptides) to be bound by the same antibody. Furthermore, it is to be understood that the two or more antigen molecules comprising the antigenic determinant capable of being bound by the same antibody can be, for example, the same molecules or fragments thereof, variants of one another, or different molecules. By way of example with reference to polypeptides comprising a cross-reactive antigenic determinant capable of being bound by the same antibody, the polypeptides can have the same or a different primary amino acid sequence, however, the polypeptides each comprise an antigenic determinant (e.g., "cross-reactive") that can be bound by the same antibody.

The term "derived from" used herein refers to an origin or source, and may include naturally occurring, recombinant, unpurified or purified molecules. The molecules of the present disclosure may be derived from viral or non-viral molecules. A protein or polypeptide derived from an original protein or polypeptide may comprise the original protein or polypeptide, in part or in whole, and may be a fragment or variant of the original protein or polypeptide. In some embodiments the RNA replicon is substantially a viral genome, meaning that the sequence contains sufficient genetic information for the replicon to autonomously replicate within a host cell or treated organism, but is not a complete wild-type viral genome.

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

By "immune response" or "immunity" as the terms are interchangeably used herein, is meant the induction of a humoral response (e.g., B cell) and/or cellular response (e.g., T cell). Suitably, a humoral immune response may be assessed by measuring the antigen-specific antibodies present in serum of immunized animals in response to introduction of one or more antigens into the host. In some exemplary embodiments below, the immune response is assessed by the enzyme-linked immunospot (ELISpot) assays on splenocytes derived from immunized animals, or by the enzyme-linked immunosorbant assay (ELISA) of sera of immunized animals, as discussed in Example 1 below. The term "immunogen" or "immunogenic" refers to a molecule that induces a specific immune response.

The terms "modified" and "sequence modification" as used herein in relation to nucleic acid molecules, polypeptides, and RNA replicons are intended to define nucleic acid molecules, polypeptides, and RNA replicons which differ in nucleotide sequence or amino acid sequence from the native (e.g., wild-type or unmodified). The terms "naturally-occurring" and "wild-type", as used herein, refer to a form found in nature. For example, a naturally occurring, unmodified, or wild-type nucleic acid molecule, nucleotide sequence, RNA replicon, or protein may be present in and isolated from a natural source, and is not intentionally modified by human manipulation. As described in detail below, the nucleic acid molecules, polypeptides, and RNA replicons according to some embodiments of the present disclosure are modified nucleic acid molecules, polypeptides, and RNA replicons, and therefore they are non-naturally occurring RNA replicons.

The terms "prime" and "boost" are intended to have their ordinary meanings in the art. "Priming" refers to immunizing a subject with a first antigenic composition to induce an immunity of the subject to an antigen that can be recalled upon subsequent exposure(s) to the same antigen or similar antigen. In some embodiments, priming induces a higher level of immune response to the antigen upon subsequent immunization ("boosting") with the same antigenic composition or with a related antigenic composition (e.g., a composition comprising an antigen having at least one cross-reactive antigenic determinant) than the immune response level obtained by immunization with a single antigenic composition, e.g., the priming composition alone or the boosting composition alone. "Booster dose" refers to an administration of an antigenic composition (e.g., a vaccine) after an earlier (prime) dose. After initial immunization (e.g., administration of a priming composition) to a subject, in some embodiments, a booster dose can be administered one or more times to the same subject for re-exposure to the same immunogenic antigen or an antigen having at least one cross-reactive antigenic determinant with the antigen used in the priming composition.

The terms "RNA replicon" and "replicon RNA" used interchangeably herein, refer to RNA which contains all of the genetic information required for directing its own amplification or self-replication within a permissive cell. To direct its own replication, the RNA molecule 1) encodes polymerase, replicase, or other proteins which may interact with viral or host cell-derived proteins, nucleic acids or ribonucleoproteins to catalyze the RNA amplification process; and 2) contain cis-acting RNA sequences required for replication and transcription of the subgenomic replicon-encoded RNA. These sequences may be bound during the process of replication to its self-encoded proteins, or non-self-encoded cell-derived proteins, nucleic acids or ribonucleoproteins, or complexes between any of these components. In some embodiments, a modified RNA replicon molecule typically contains the following ordered elements: 5' viral RNA sequence(s) required in cis for replication, sequences coding for biologically active nonstructural proteins, promoter for the subgenomic RNA, 3' viral sequences required in cis for replication, and a polyadenylate tract. Further, the RNA replicon can be a molecule of positive polarity, or "message" sense, and the RNA replicon may be of length different from that of any known, naturally-occurring RNA viruses. In some embodiments of the present disclosure, the RNA replicon can lack or functionally lack at least one of the sequences of the structural viral proteins present in wild-type virus genomes. By functionally lack is meant that the structural viral proteins are not present in an amount or in a form that permits them to perform their usual and natural function. In many embodiments the sequences encoding structural genes can be substituted with one or more heterologous sequences such as, for example, a sequence encoding a gene of interest (GOI). In some embodiments the GOI can be, for example, a sequence encoding a polypeptide that is an antigen or antigenic determinant to the subject patient (such as an antigen described herein), an antibody, or a fragment of an antibody. In those instances where the RNA replicon is to be packaged into a recombinant alphavirus particle, it must contain one or more sequences, so-called packaging signals, which serve to initiate interactions with alphavirus structural proteins that lead to particle formation. The RNA replicons of the invention can have the ability to self-amplify and can self-amplify within a host cell or animal cell. In various embodiments the RNA replicons can be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size. "Fragments" of a molecule (e.g. a nucleic acid, polypeptide, or antibody molecule) can contain at least at least 10 or at least 20 or at least 30 or at least 50 or at least 75 or at least 100 or at least 200 or at least 300 or at least 500 or at least 1 kb or at least 2 kb or at least 3 kb or at least 5 kb nucleotides for a nucleic acid, or amino acids for a polypeptide molecule. A fragment can also be a binding domain of a specific binding molecule. In some embodiments the RNA replicons are not viral vectors, which utilize viral proteins (e.g. a capsid protein encoded on the viral vector) to deliver its nucleic acid into a host cell. The RNA replicons of the invention can lack, functionally lack, or not have a capsid or viral particle, or can not be encapsidated in a capsid or comprised in a viral particle.

The RNA replicons of the invention can be derived from a naturally occurring or wild-type virus (e.g. an RNA virus or retrovirus described herein), meaning that the replicon has been modified from a wild-type viral genome. The RNA replicons of the invention can include sequences not present in a wild-type viral genome, for example one or more heterologous sequence(s) (e.g. one or more gene(s) of interest) and/or other sequences or modifications as described herein. The RNA replicons can also have one or more sequences deleted or functionally deleted from a wild-type genome (e.g. viral structural proteins). A sequence is functionally deleted when it is not present in an amount or in a form that permits it to perform its usual and natural function. For example a sequence can be deleted completely or substantially, or otherwise shortened so that it does not perform its usual and natural function. In different embodiments the RNA replicons of the invention can have at least at least 50% or at least 60% or at least 70% or at least 80% or at least 90% or at least 95% or 80-99% or 90-95% or 90-99% or 95-99% or 97-99% or 98-99% sequence identity with a sequence of a wild type genome. In some embodiments the percent of sequence identity can be calculated while not counting one or more heterologous sequence(s) that may be present on the replicon (e.g. a gene of interest), and/or not counting the deletion of one or more sequences that would be naturally present in the wild-type genome (e.g. one or more structural genes).

In some embodiments, the RNA replicons disclosed herein are engineered, synthetic, or recombinant RNA replicons. As used herein, the term recombinant means any molecule (e.g. DNA, RNA, etc.), that is, or results, however indirect, from human manipulation of a polynucleotide. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant RNA replicon can be one or more of the followings: 1) synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules; 2) conjoined nucleotide sequences that are not conjoined in nature; 3) engineered using molecular cloning techniques such that it lacks one or more nucleotides with respect to the naturally occurring nucleotide sequence; and 4) manipulated using molecular cloning techniques such that it has one or more sequence changes or rearrangements with respect to the naturally occurring nucleotide sequence.

The term "variant" of a protein used herein refers to a polypeptide having an amino acid sequence that is the same or essentially the same as that of the reference protein except having at least one amino acid modified, for example, deleted, inserted, or replaced, respectively. The amino acid replacement may be a conservative amino acid substitution, preferably at a non-essential amino acid residue in the protein. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, and histidine), acidic side chains (e.g., aspartic acid, and glutamic acid), uncharged polar side chains (e.g., glycine, asparagine, glutamine, serine, threonine, tyrosine, and cysteine), non-polar side chains (e.g., alanine, valine, leucine, isoleucine, proline, phenylalanine, methionine, and tryptophan), beta-branched side chains (e.g., threonine, valine, and isoleucine) and aromatic side chains (e.g., tyrosine, phenylalanine, tryptophan, and histidine). A variant of a protein may have an amino acid sequence at least about 80%, 90%, 95%, 98%, or 99%, preferably at least about 90%, more preferably at least about 95%, identical to the amino acid sequence of the protein. Preferably, a variant is a functional variant of a protein that retains the same function as the protein.

Also of interest of the present disclosure are variants of the polynucleotides described herein. Such variants may be naturally-occurring, including homologous polynucleotides from the same or a different species, or may be non-natural variants, for example polynucleotides synthesized using chemical synthesis methods, or generated using recombinant DNA techniques. With respect to nucleotide sequences, degeneracy of the genetic code provides the possibility to substitute at least one base of the protein encoding sequence of a gene with a different base without causing the amino acid sequence of the polypeptide produced from the gene to be changed. Hence, the polynucleotides of the present disclosure may also have any base sequence that has been changed from any polynucleotide sequence disclosed herein by substitution in accordance with degeneracy of the genetic code. References describing codon usage are readily publicly available. In further embodiments, polynucleotide sequence variants can be produced for a variety of reasons, e.g., to optimize codon expression for a particular host (e.g., changing codons in the viral mRNA to those preferred by other organisms such as mammals or fish species).

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

In some embodiments of the methods or processes described herein, the steps can be carried out in any order, except when a temporal or operational sequence is explicitly recited. Furthermore, in some embodiments, the specified steps can be carried out concurrently unless explicit claim language recites that they be carried out separately. For example, in some embodiments a claimed step of doing X and a claimed step of doing Y can be conducted simultaneously within a single operation, and the resulting process will fall within the literal scope of the claimed process.

As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", for example in a description of components of a composition or in a description of steps of a method, is understood to encompass those compositions and methods consisting essentially of and consisting of the recited components or steps.

Headings, e.g., (a), (b), (c), etc., are presented merely for ease of reading the specification and claims, and do not limit in any way the scope of the disclosure or its alternatives. The use of headings in the specification or claims does not require the steps or elements be performed in alphabetical or numerical order or the order in which they are presented.

Methods for Heterologous Prime-Boost Immunization

Multi-dose immunization, for therapy or for disease prevention, has been reported to be often more effective than single-dose immunization. It is generally believed that generating a high number of antigen-specific memory CD8 T cells following vaccination is a desirable goal for vaccine design against a variety of animal and human diseases, because this number strongly correlates with host immunization and protection. One approach to generate these high numbers of cells is to use a process of prime-boost immunization, which relies on the re-stimulation of antigen-specific immune cells following primary memory formation. In such a process, there is a "priming" composition which is administered to the subject first and a "boosting" composition which is subsequently administered one or more times. Without being bound by any particular theory, it is widely believed that boosting of immune responses by vaccines results in generation of larger numbers of effector cells required for mediating protection against pathogens at the time of infection.

Homologous prime-boost immunizations that utilize re-administration of the same immunization agent have been used since the initial development of vaccines. Classic vaccination approaches relied on a homologous prime-boost regime and have traditionally been unable to elicit immune responses strong enough to tackle more challenging diseases. For example, although this method is usually effective in boosting the humoral response to antigen, it has been generally considered to be far less effective at generating increased numbers of CD8 T cells due to rapid clearance of the homologous boosting agent by the primed immune system, and further fail to boost cellular immunity (CMI).

On the other hand, heterologous prime-boost immunization, or the administration of the same immunogen using two different modalities, was recently developed as a strategy to elicit superior immune responses in subjects. In particular, new vaccine modalities, such as heterologous prime-boosts, have been successfully employed against complex pathogens such as malaria, Tuberculosis (TB), human immunodeficiency virus (HIV), and Ebola. Superior memory responses resulting from heterologous prime-boost immunization include, but are not limited to, a higher magnitude of CD8+ T cell responses, a broadening of T cell epitopes recognized by the immune system, and an increase in polyfunctionality of T cells. In some embodiments the prime-boost methods of the invention result in a significant increase in IFN-γ-secreting CD8+ T cells in the treated subject. In various embodiments the significant increase can be an increase of at least 25% or at least 50% or at least 100% or at least 150% or at least 200% or at least 250% or at least 300% versus single dose administration or versus a homologous prime-boost regimen. In addition, a heterologous prime-boost approach is reported to effectively boost CMI, especially when vector-based vaccine candidates are used, as it minimizes the interference by anti-vector immunity generated after priming. Apart from enhancing the effector cells quantitatively, qualitative differences in secondary memory cells are also seen after the boosting. Secondary memory CD8 T cells, in contrast to primary memory cells, traffic much more efficiently to peripheral tissues and exhibit enhanced cytolysis facilitating effective countering of pathogens at the site of entry. Additionally, a heterologous prime-boost strategy can result in synergistic enhancement of immune response resulting in an increased number of antigen-specific T cells, selective enrichment of high avidity T cells and increased breadth as well as depth of the immune response. By way of example, FIG. 1 schematically depicts benefits of heterologous prime-boost regimens in that they can result in improving both the magnitude, length, and the quality of the immune memory response (figure adapted from Nolz J C and Harty J T, *Adv. Exp. Med. Biol.,* 2011). In this example, booster vaccinations are used to generate increased numbers of memory CD8 T cells. The magnitude of immune response to a traditional prime-boost regimen or to a heterologous prime-boost regimen, as determined by total number of antigen specific CD8

T cells, is plotted over time. Following primary vaccine challenge, CD8 T cells undergo expansion, contraction, and form a primary memory population. When this primary memory population of CD8 T cells is exposed to a secondary challenge of the same vaccination (homologous boost, dashed line), another round of expansion, contraction and formation of a larger, secondary memory population occurs. In contrast to a homologous booster vaccination, administration of a CD8 T cell antigen delivered in the context of a different vector (heterologous boost, solid line) drives greater expansion of the primary memory CD8 T cells, resulting in a larger secondary memory population than what is seen with homologous booster vaccinations.

While heterologous prime-boosts have been reported to increase responses in certain settings, not all combinations demonstrate improved immunity showing the importance of determining which combinations are effective. Finding vaccine combinations that elicit broad, durable, and long-lasting immunity are important for conferring robust protection. More specifically, Alphavirus-derived replicons such as, for example, Sindbis virus, VEE virus, and Semliki-forest virus, have all been employed in heterologous prime-boost settings in combination with protein, DNA, and virosomes. These have proven to be effective in immunizing small animal models, such as mice, for human papillomavirus (HPV) and human immunodeficiency virus (HIV), as well as in NHPs with the replicon being delivered in the particle form for Dengue. Furthermore, fully synthetic alphavirus-derived replicons have been used extensively in homologous prime-boost regimes. Previously, the only fully synthetic replicon system that has been widely employed has been derived from the Alphavirus family of viruses, wherein the non-structural proteins have been retained and the structural proteins have been replaced with a gene of interest. However, recent advances in engineering of new replicons have resulted in the production of novel types of replicon and have permitted discovering novel vaccine modalities using only synthetic replicons.

Similarly, classic approaches to therapeutic administration of proteins have traditionally relied on exogenous injection of proteins in high enough doses to have the desired clinical effect. More recently, nucleic acid or viral-based vectors have been used to deliver a sequence to a host cell resulting in the expression of a desired protein of interest. However, strictly nucleic acid-based delivery methods such as mRNA, while relatively non-immunogenic, do not have durable and persistent expression of protein. In contrast, viral-derived methods are capable of more durable and persistent protein expression, but are also inherently immunogenic. This can result in immune responses against the cells producing the protein, and sometimes the protein itself in the form of anti-drug antibodies. Viral-based methods of protein delivery also tend to have higher costs and more complex manufacturing, limiting how broadly this technique can be employed. For this reason, using replicons with immunologically different mechanisms of activating the immune system may allow an increased or more varied number of repeated injections allowing for the more persistent expression of therapeutic proteins. This approach would also be expected to help limit the formation of anti-drug antibodies that reduce the level of therapeutic protein being produced.

In one aspect, various embodiments of the disclosure generally relate to methods for delivering two RNA replicons into a subject for therapeutic and/or prophylactic applications such as, for example, vaccination and/or immunization applications. In one aspect, some embodiments disclosed herein relate to a method for inducing an immune response in a subject, the method includes administering to the subject at least one dose of a priming composition comprising a first RNA replicon which encodes a first antigen; and subsequently administering to the subject at least one dose of a boosting composition comprising a second RNA replicon which encodes a second antigen, wherein the first and second RNA replicons are different from each other. In some embodiments, the first antigen and the second antigen are identical to each other. In some embodiments, amino acid sequences of the first and the second antigens are homologous to each other. In some embodiments the first RNA replicon and second RNA replicon are derived from genomes of RNA viruses of different genera. In some embodiments, the amino acid sequence of the first antigen exhibits at least 80%, 85%, 90%, 95%, 96%, 97%, 98%, or 99% sequence identity to the amino acid sequence of the second antigen. In some embodiments, the first and the second antigens comprise at least one cross-reactive antigenic determinant. In some embodiments, the first and the second antigens induce substantially the same immune response in the subject.

In some embodiments, the priming composition is administered into the subject in a single dose. In some embodiments, the priming composition is administered into the subject in multiple doses. In some embodiments, the boosting composition is administered into the subject in a single dose. In some embodiments, the boosting composition is administered into the subject in multiple doses. In some embodiments, the priming composition and/or the boosting composition is administered to the subject for at least 2, at least 3, at least 4, at least 5, or at least 10 consecutive dosages or any number dosage therebetween. In some embodiments, the priming composition and/or the boosting composition is administered to the subject for at least 10, at least 12, at least 14, at least 16, or at least 20 consecutive dosages or any number dosage therebetween. Without being bound to any particular theory, it is generally believed that higher antigen doses at priming generally favor the induction of effector cells, whereas lower doses may preferentially drive the induction of immune memory. Hence, higher dose of a priming composition, although desirable for immediate responses, may affect development of memory cells and adversely hamper the effect of high dose. Contrary to the prime dose, higher dose of the boost composition has been shown to induce higher magnitude of immune response as the greater availability of antigen might be driving higher number of memory B cells into differentiation, thereby amplifying the response. In some embodiments, the priming composition and/or the boosting composition can be administered into the subject in multiple dosages ranging from about 0.001 mg/kg body weight to about 50 mg/kg body weight. This dose range is equivalent to about 0.025 µg to 50 µg of RNA replicon in formulated state for a 25 g mouse. In some embodiments, preferred doses of the priming composition and/or the boosting composition comprise less than 1 µg of RNA replicon in formulated state. In some embodiments, preferred doses of the priming composition and/or the boosting composition comprise about 100 µg, about 200 µg, about 300 µg, about 400 µg, about 500 µg, about 600 µg, about 700 µg of RNA replicon in non-formulated state (e.g., naked RNA in saline solution). In various embodiments either or both of the first and second RNA replicons can be administered as naked RNA (e.g. in saline) or either or both can be administered comprised in a nano-particle; or either one can be administered as naked RNA and the other administered in a nano-particle. In some embodiments wherein small animal models are involved, the priming composition and/or the boosting composition can be administered into the subject in one or more dosages ranging from about 0.01 µg to about 30 µg. In some embodiments wherein large animal models and humans are involved, the priming composition and/or the boosting composition can be administered into the subject in one or more dosages ranging from about 0.1 µg to about 100 µg. In some embodiments, suitable doses for small animal models range from about $5 \times 10^{-5}$ µg/100 mg to about 0.15 µg/100 mg. This dose range is equivalent to about 0.01 µg to about 30 µg for a 20 g mouse. In some embodiments, the priming composition and/or the boosting composition is administered into the subject in multiple dosages of about 15 µg per dose for a 20 g mouse. In some embodiments, for large animal models, such as, for example humans, suitable dosages range from about $1.25 \times 10^{-7}$ µg/100 mg to $1.25 \times 10^{-4}$ µg/100 mg. This dose range is equivalent to about 0.1 µg to about 100 µg doses for an 80 kg host. In some embodiments, the priming composition and/or the boosting composition is administered into the subject in multiple dosages of about 0.001 µg, about 0.01 µs, about 0.1 µg, about 1 µg, about 10 µg, about 100 µg, about 200 µg, about 300 µg of RNA per whole body dose in formulated state. In some embodiments, the priming composition and/or the boosting composition is administered into the subject in multiple dosages of about 50 µg of RNA per whole body dose. In some embodiments, the priming composition and/or the boosting composition is administered in gradually increasing dosages over time. In some embodiments, the priming composition and/or the boosting composition is administered in gradually decreasing dosages over time.

In some embodiments of methods disclosed herein, immunization schedule can be important. For example, a delayed boosting will be helpful in avoiding interference in the primary responses induced by the prime. Although closely spaced (e.g., 1-2 weeks) vaccine doses can cause a rapid induction of immune response, in some embodiments, the response may be less persistent than when the same numbers of vaccine doses were given at longer intervals (e.g., 1-2 months). A minimal interval of 1-2 weeks may also ensure optimal affinity maturation of memory B cells. In some embodiments of the methods disclosed herein, the at least one dose of the priming composition and the boosting composition are administered into the subject at intervals of about 1 week, or 2, 3, 4, 5, 6, 7, or 8 or 1-2 or 2-4 or 3-4 weeks. In some embodiments of the methods disclosed herein, the at least one dose of the priming composition and the boosting composition are administered into the subject at intervals of about 4 weeks. One of skill in the art will further appreciate that for any particular subject, specific dosage regimens can be adjusted over time according to the individual need and the professional judgment of the person administering or supervising the administration of the compositions. For example, doses may be adjusted based on clinical effects of the administered compositions such as toxic effects and/or laboratory values. Dosage regimens can be adjusted to provide the optimal desired effect. For example, as discussed above, a single dose can be administered, several divided doses can be administered over time or the dose can be proportionally reduced or increased as indicated by the exigencies of the therapeutic situation. Determining appropriate dosages and regimens for administration of the compositions disclosed herein are well-known in the relevant art and would be understood to be encompassed by the skilled artisan once provided the teachings disclosed herein.

Thus, a person of skill in the art would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject can also be determined, as can the temporal requirements for administering each agent to provide a detectable therapeutic benefit to the patient. Accordingly, while certain dose and administration regimens are exemplified herein, these examples in no way limit the dose and administration regimen that can be provided to a patient in practicing the present disclosure.

Administration of the priming and boosting compositions disclosed herein may be affected by any method that enables delivery of the compositions to the site of action. These methods include oral routes, intraduodenal routes, parenteral injection (comprising intravenous, subcutaneous, intramuscular, intravascular, or infusion), topical administration, and rectal administration. Infusions can be administered by drip, continuous infusion, infusion pump, metering pump, depot formulation, or any other suitable means. In some embodiments, at least one dose of the priming composition is administered intramuscularly to the subject. In some embodiments, at least one dose of the boosting composition is administered intramuscularly to the subject.

In some embodiments, the at least one dose of boosting composition comprises different types of antigen comprising at least one cross-reactive epitope. In some embodiments, the method for heterologous prime-boost immunization disclosed herein intends to encompass immunization regimens in which one of the multiple boosting compositions comprises the same RNA replicon as used in the priming composition and thus a "homologous boost," either of the same or different doses, as long as at least one of the multiple administrations of the boosting composition comprises a RNA replicon that is different from that used in the priming composition.

In some embodiments, the first antigen in the priming composition can be the same antigen as the second antigen in the boosting composition. In some embodiments, the first antigen and the second antigen have the same amino acid sequence. In some embodiments, the amino acid sequence of the first antigen is a portion (for example, at least 80%, 85%, 90%, 95%, 96%, 97%, 98%, or 99%) of the amino acid sequence of the second antigen. In some embodiments, the first and the second antigens comprise amino acid sequences that are homologous (for example substantially identical) to each other. The term "identical" or "percent identity" as used herein in the context of two or more polymeric molecules, e.g., amino acid sequences of polypeptides, refers to the sequence similarity between the polymeric molecules. Two amino acid sequences are homologous (e.g., substantially identical) if there is a partial or complete identity between their sequences. For example, 80% identical means that 80% of the amino acids are identical when the two sequences are aligned for maximum matching. As such, the term "substantially identical" refers to a first amino acid which contains a sufficient or minimum number of identical or equivalent (e.g., with similar side chain) amino acids to a second amino acid sequence such that the first and the second amino acid sequences have a common domain, such as an immunologically antigenic determinant (e.g., epitope). For example, the amino acid sequence of the first antigen can exhibit 80%, 85%, 90%, 95%, 96%, 97%, 98%, 99%, 100%, or a range between any two of these values, sequence identity to the amino acid sequence of the second antigen. In some embodiments, the amino acid sequence of the first antigen exhibits at least 80%, at least 90%, at least 95%, at least 96%, at least 97%, at least 98%, at least 99%, or 100% sequence identity to the amino acid sequence of the second antigen. In some embodiments, the amino acid sequence of the first antigen exhibits at least 80% sequence identity to the amino acid sequence of the second antigen. In some embodiments, the amino acid sequence of the first antigen exhibits at least 90% sequence identity to the amino acid sequence of the second antigen. In some embodiments, the amino acid sequence of the first antigen exhibits at least 95% sequence identity to the amino acid sequence of the second antigen. In some embodiments, the amino acid sequence of the first antigen exhibits at least 98% sequence identity to the amino acid sequence of the second antigen. In some embodiments, the amino acid sequence of the first antigen exhibits at least 99% sequence identity to the amino acid sequence of the second antigen. In some embodiments, the amino acid sequence of the first antigen exhibits at least 100% sequence identity to the amino acid sequence of the second antigen. In some embodiments, the amino acid sequence of the first antigen is identical to the amino acid sequence of the second antigen.

As used herein, the terms, "identical" or percent "identity", in the context of two or more nucleic acid sequences or polypeptide sequences, refer to two or more sequences or subsequences that are the same or have a specified percentage of amino acid residues or nucleotides that are the same, when compared and aligned for maximum correspondence over a comparison window. Unless otherwise specified, the comparison window for a selected sequence, e.g., "SEQ ID NO: X" is the entire length of SEQ ID NO: X, and, e.g., the comparison window for "100 bp of SEQ ID NO: X" is the stated 100 bp. The degree of amino acid or nucleic acid sequence identity can be determined by various computer programs for aligning the sequences to be compared based on designated program parameters. For example, sequences can be aligned and compared using the local homology algorithm of Smith & Waterman *Adv. Appl. Math.* 2:482-89, 1981, the homology alignment algorithm of Needleman & Wunsch *J. Mol. Biol.* 48:443-53, 1970, or the search for similarity method of Pearson & Lipman *Proc. Nat'l. Acad. Sci. USA* 85:2444-48, 1988, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-87, 1993). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

In some embodiments, the first and the second antigens comprise at least one cross-reactive antigenic determinant. The term "epitope" or "antigenic determinant", as used interchangeably herein, refers to the primary, secondary, tertiary, or quaternary structure of an antigenic molecule (e.g., a polypeptide) recognized by B cells (e.g., B lymphocytes) and the antibodies secreted by B cells. Epitopes can be linear or conformational. Generally, an epitope includes at least 3, 4, 5, 6, 7, 8, 9, 10, 11, 12, 13, 14, or 15 consecutive or non-consecutive amino acids in a unique spatial conformation. Encompassed by the term "epitope" and "antigenic determinant" are simple epitopes, which comprise only a few contiguous amino acid residues, as well as complex epitopes that encompass discontinuous amino acid residues. In some cases, complex epitopes comprise amino acid residues separated in the primary sequence but in close proximity in the three-dimensional folded structure of an antigen. The term "cross-reactive antigenic determinant" "or cross-reactive epitope" refers to the ability of an antigenic determinant present on two or more antigen molecules (e.g., polypeptides) to be bound by the same antibody. Furthermore, it is to be understood that the two or more molecules comprising the antigenic determinant capable of being bound by the same antibody can be, for example, the same molecules or fragments thereof, variants of one another, or different molecules. By way of example with reference to polypeptides comprising an antigenic determinant capable of being bound by the same antibody, the polypeptides can have the same or a different primary amino acid sequence, however, the polypeptides each comprise an antigenic determinant (e.g., "cross-reactive") that can be bound by the same antibody. In some embodiments, the first and the second antigens induce substantially the same immune response in the subject. In some embodiments, the term "substantially the same immune response" can refer to, for example, where the concentration of antibodies induced against the first antigen is about the same, or at least about 75%, or at least about 80%, or at least about 90%, or at least about 95%, or at least about 99% of the concentration of antibodies induced against the second antigen tested under the same conditions. In some embodiments, the first and the second antigens induce the same immune response in the subject, e.g., the concentration of antibodies induced against the first antigen is identical to the concentration of antibodies induced against the second antigen tested under the same conditions.

In some embodiments, the term "substantially the same immune response" can refer to, for example, where the type of antibody profile induced against the first antigen is about the same, or at least about 75%, or at least about 80%, or at least about 90%, or at least about 95%, or at least about 99% identical to the type of antibody profile induced against the second antigen tested under the same conditions. In some embodiments, the first and the second antigens induce the same immune response in the subject, e.g., the type of antibody profile induced against the first antigen is identical to the type of antibody profile induced against the second antigen tested under the same conditions.

In some embodiments disclosed herein, the first and the second RNA replicons are capable of activating an immune system of the subject through different immunological mechanisms, e.g. differentially engaging or activating the immune system of a subject patient. For example, in some embodiments, the first RNA replicon can activate the immune system of the subject through an immunological mechanism that is different from one or more, or any, of the immunological mechanisms that the second RNA replicon is capable of activating the immune system in the subject. In some embodiments, each of the first and second RNA replicons may independently be capable of activating the immune system of the subject through one, two, three, or more immunological mechanisms. In some embodiments, the first and second RNA replicons can activate the immune system through one, two, three, or more common immunological mechanisms; however, at least one of the immunological mechanisms utilized by the first RNA replicon is different from each of the immunological mechanisms utilized by the second RNA replicon. Non-limiting examples of immunological mechanisms through which the first and/or the second replicons can activate the immune system include (1) different active mechanisms of host cell immune evasion encoded by non-structural proteins of a distinct or related replicon; (2) different passive mechanisms for the host cell immunity to recognize the replicon itself; and (3) co-encoding of immune modulating proteins that function to differentially engage or activate the immune system during the first and second injection. In some embodiments of the disclosure, the at least one of the two or more immunological mechanisms is selected from the group consisting of differential activation of protein kinase R (PKR), retinoic acid-inducible gene I (RIG-I), autophagy pathways, Toll-like receptors (TLRs), stress granules, RNase R, and oligoadenylate synthetases (OAS).

In some embodiments, at least one of the first and second RNA replicons is a modified replicon. In some embodiments, the first and second RNA replicons are derived from a positive-strand RNA virus. In some embodiments, at least one of the first and second RNA replicons is derived from a virus species belonging to a family selected from the group consisting of Togaviridae family, Flaviviridae family, Orthomyxoviridae family, Rhabdoviridae family, Arteriviridae family, Picornaviridae family, Astroviridae family, Coronaviridae family, and Paramyxoviridae family. Accordingly, in some embodiments, at least one of the first and second RNA replicons is derived from a negative-strand RNA virus. Suitable negative-strand RNA virus species include, but are not limited to viral species of the families Orthomyxoviridae, Rhabdoviridae, and Paramyxoviridae. In some embodiments, at least one of the first and second RNA replicons is derived from a virus species belonging to the Orthomyxoviridae family. In some embodiments, at least one of the first and second RNA replicons is derived from a virus species belonging to a Orthomyxovirus genus selected from the group consisting of Influenza virus A, Influenza virus B, Influenza virus C, Influenza virus D, Isavirus, Thogotovirus and Quaranjavirus. In some embodiments, at least one of the first and second RNA replicons is derived from an Influenza virus. In some embodiments, at least one of the first and second RNA replicons is derived from an Influenza virus A.

In some embodiments, at least one of the first and second RNA replicons is derived from a virus species belonging to the Rhabdoviridae family. In some embodiments, at least one of the first and second RNA replicons is derived from a virus species belonging to a Rhabdovirus genus selected from the group consisting of Curiovirus, Cytorhabdovirus, Dichorhavirus, Ephemerovirus, Hapavirus, Ledantevirus, Lyssavirus, Novirhabdovirus, Nucleorhabdovirus, Perhabdovirus, Sigmavirus, Sprivivirus, Sripuvirus, Tibrovirus, Tupavirus, Varicosavirus, Vesiculovirus. Non-limiting examples of preferred Rhabdovirus species include, but are not limited to, viral hemorrhagic septicemia virus (VHSV), vesicular stomatitis virus (VSV), and rabies virus (RABV).

In some embodiments, at least one of the first and second RNA replicons is derived from a virus species belonging to the Paramyxoviridae family. In some embodiments, at least one of the first and second RNA replicons is derived from a Paramyxovirus virus species belonging to the Pneumovirinae subfamily or the Paramyxovirinae subfamily. In some embodiments, at least one of the first and second RNA replicons is derived from a virus species belonging to a Paramyxovirus genus selected from the group consisting of Aquaparamyxovirus, Avulavirus, Ferlavirus, Henipavirus, Metapneumovirus, Morbillivirus, Pneumovirus, Respirovirus, and Rubulavirus. Non-limiting examples of preferred Paramyxovirus species include, but are not limited to, human respiratory syncytial virus (hRSV, subgroup A), bovine respiratory syncytial virus (bRSV), human metapneumovirus (hMPV), bovine-human parainfluenza virus 3 (b/hPIV3), human parainfluenza virus 1 (hPIV1), recombinant bovine-human parainfluenza virus 3 (rB/HPIV3), Sendai virus (SeV), Andes virus (ANDV), Mumps virus (MuV), Simian virus 5 (SV5), and Measles virus (MeV).

In some embodiments, at least one of the first and second RNA replicons is derived from a positive-strand virus species belonging to the Togaviridae family or Flaviviridae family. In some embodiments, at least one of the first and second RNA replicons is derived from a virus species belonging to the Flaviviridae family such as, for example, viruses belonging to the genera Flavivirus and Pestivirus. Non-limiting examples of viruses belonging to the genus Flavivirus include yellow fever virus (YFV), Dengue fever virus, Japanese encephalitis virus (JEV), West Nile virus (WNV) and Zika virus. In some embodiments, at least one of the first and second RNA replicons is derived from yellow fever virus or Dengue fever virus. Virulent and avirulent flavivirus strains are both suitable. Non-limiting examples of preferred flavivirus strains include, but are not limited to, YFV (17D), DEN4 (814669 and derivatives), DEN2 (PDK-53), Kunjin virus (KUN), JEV (SA14-14-2), Murray Valley encephalitis virus (MVEV, with IRES attenuated), WNV (SCFV), Bovine viral diarrhea virus (BVDV) CP7, BVDV-SD1, BVDV-NADL, and classical swine fever virus (CSFV).

In some embodiments, at least one of the first and second RNA replicons is derived from a positive-strand virus species, for example a virus species belonging to the Alphavirus genus of the Togaviridae family. In some embodiments, at least one of the first and second RNA replicons is derived from a positive-strand virus species belonging to the Arterivirus genus of the Arteriviridae family. In some embodiments, at least one of the first and second RNA replicons is derived from a positive-strand virus species belonging to the Arterivirus genus of the Arteriviridae family and the other RNA replicon is derived from a species belonging to the Alphavirus genus of the Togaviridae family.

Alphaviruses

Alphavirus is a genus of genetically, structurally, and serologically related viruses of the group IV Togaviridae family which includes at least 30 members, each having single stranded RNA genomes of positive polarity enclosed in a nucleocapsid surrounded by an envelope containing viral spike proteins. Currently, the alphavirus genus comprises among others the Sindbis virus (SIN), the Semliki Forest virus (SFV), the Ross River virus (RRV), Venezuelan equine encephalitis virus (VEEV), and Eastern equine encephalitis virus (EEEV), which are all closely related and are able to infect various vertebrates such as mammals, rodents, fish, avian species, and larger mammals such as humans and horses as well as invertebrates such as crustaceans and insects. Transmission between species and individuals occurs mainly via mosquitoes making the alphaviruses a contributor to the collection of Arboviruses—or Arthropod-Borne Viruses. For example, the Sindbis and the Semliki Forest viruses have been widely studied and the life cycle, mode of replication, etc., of these viruses are well characterized. For example, alphaviruses have been shown to replicate very efficiently in animal cells which makes them valuable as vectors for production of protein and nucleic acids in such cells.

Alphavirus particles are enveloped, have a 70 nm diameter, tend to be spherical (although slightly pleomorphic), and have an approximately 40 nm isometric nucleocapsid. The Alphavirus genome is single-stranded RNA of positive polarity of approximately 11-12 kb in length, comprising a 5' cap, a 3' poly-A tail, and two open reading frames with a first frame encoding the nonstructural proteins with enzymatic function and a second frame encoding the viral structural proteins (e.g., the capsid protein C, E1 glycoprotein, E2 glycoprotein, E3 protein and 6K protein).

The 5' two-thirds of the alphavirus genome encodes a number of nonstructural proteins necessary for transcription and replication of viral RNA. These proteins are translated directly from the RNA and together with cellular proteins form the RNA-dependent RNA polymerase essential for viral genome replication and transcription of subgenomic RNA. Four nonstructural proteins (nsP1-4) are produced as a single polyprotein and constitute the virus' replication machinery. The processing of the polyprotein occurs in a highly regulated manner, with cleavage at the P2/3 junction influencing RNA template use during genome replication. This site is located at the base of a narrow cleft and is not readily accessible. Once cleaved, nsP3 creates a ring structure that encircles nsP2. These two proteins have an extensive interface. Mutations in nsP2 that produce noncytopathic viruses or a temperature sensitive phenotypes cluster at the P2/P3 interface region. P3 mutations opposite the location of the nsP2 noncytopathic mutations prevent efficient cleavage of P2/3. This in turn can affect RNA infectivity altering viral RNA production levels.

The 3' one-third of the genome comprises subgenomic RNA which serves as a template for translation of all the structural proteins required for forming viral particles: the core nucleocapsid protein C, and the envelope proteins P62 and E1 that associate as a heterodimer. The viral membrane-anchored surface glycoproteins are responsible for receptor recognition and entry into target cells through membrane fusion. The subgenomic RNA is transcribed from the p26S subgenomic promoter present at the 3' end of the RNA sequence encoding the nsp4 protein. The proteolytic maturation of P62 into E2 and E3 causes a change in the viral surface. Together the E1, E2, and sometimes E3, glycoprotein "spikes" form an E1/E2 dimer or an E1/E2/E3 trimer, where E2 extends from the center to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphaviral glycoprotein E1 is a class II viral fusion protein, which is structurally different from the class I fusion proteins found in influenza virus and HIV. The E2 glycoprotein functions to interact with the nucleocapsid through its cytoplasmic domain, while its ectodomain is responsible for binding a cellular receptor. Most alphaviruses lose the peripheral protein E3, while in Semliki viruses it remains associated with the viral surface. In some embodiments the first and/or second RNA replicons do not code for any viral structural protein, or do not code for E1 or E2 or E3, or any one of them or any combination of them. For example when the RNA replicon is derived from an alphavirus it can not encode for E1 or E2 or E3, nor any combination or sub-combination of them.

Alphavirus replication is a membrane-associated process within the host cell. In the first step of the infectious cycle, the 5' end of the genomic RNA is translated into a polyprotein (nsP1-4) with RNA polymerase activity that produces a negative strand complementary to the genomic RNA. In a second step, the negative strand is used as a template for the production of two RNAs, respectively: (1) a positive genomic RNA corresponding to the genome of the secondary viruses producing, by translation, other nsp proteins and acting as a genome for the virus; and (2) subgenomic RNA encoding the structural proteins of the virus forming the infectious particles. The positive genomic RNA/subgenomic RNA ratio is regulated by proteolytic autocleavage of the polyprotein to nsp 1, nsp 2, nsp 3 and nsp 4. In practice, the viral gene expression takes place in two phases. In a first phase, there is main synthesis of positive genomic strands and of negative strands. During the second phase, the synthesis of subgenomic RNA is virtually exclusive, thus resulting in the production of large amount of structural protein.

In some embodiments disclosed herein, at least one of the first and second RNA replicons is derived from an alphavirus species. In some embodiments, the alphavirus RNA replicon is derived from an alphavirus belonging to the VEEV/EEEV group, or the SF group, or the SIN group (for review, see, e.g. Strauss and Strauss. *Microbiol. Rev.,* 58:3 p 492-562, 1994). Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S.A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Western equine encephalitis virus (WEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV). Virulent and avirulent alphavirus strains are both suitable for the methods and compositions disclosed herein. In some particular embodiments, the alphavirus RNA replicon is derived from a Sindbis virus (SIN), a Semliki Forest virus (SFV), a Ross River virus (RRV), a Venezuelan equine encephalitis virus (VEEV), or an Eastern equine encephalitis virus (EEEV). In some embodiments, the alphavirus RNA replicon is derived from a Venezuelan equine encephalitis virus (VEEV).

In some embodiments, both of the first and second RNA replicons are derived from alphavirus species. In some embodiments, the first and second RNA replicons are derived from the same alphavirus species or from two different alphavirus species. In some embodiments, the first RNA replicon is derived from an alphavirus and the second RNA replicon is derived from a non-alphavirus species. Non-limiting examples of non-alphavirus RNA replicons include RNA replicons derived from virus species belonging to a family selected from the group consisting of Togaviridae family, Flaviviridae family, Orthomyxoviridae family, Rhabdoviridae family, Arteroviridae family, Picornaviridae family, Astroviridae family, Coronaviridae family, and Paramyxoviridae family. Accordingly, in some embodiments, the non-alphavirus RNA replicon is derived from a negative-strand RNA virus. Suitable negative-strand RNA virus species include, but are not limited to viral species of the families Orthomyxoviridae, Rhabdoviridae, and Paramyxoviridae. In some embodiments, the non-alphavirus RNA replicon is derived from a negative-strand RNA virus species belonging to the Orthomyxoviridae family. In some embodiments, the non-alphavirus RNA replicon is derived from a virus species belonging to an Orthomyxovirus genus selected from the group consisting of Influenza virus A, Influenza virus B, Influenza virus C, Influenza virus D, Isavirus, Thogotovirus and Quaranjavirus. In some embodiments, the non-alphavirus RNA replicon is derived from an Influenza virus. In some embodiments, the non-alphavirus RNA replicon is derived from an Influenza virus A.

In some embodiments, the non-alphavirus RNA replicon is derived from a negative-strand RNA virus species belonging to the Rhabdoviridae family. In some embodiments, the non-alphavirus RNA replicon is derived from a virus species belonging to a Rhabdovirus genus selected from the group consisting of Curiovirus, Cytorhabdovirus, Dichorhavirus, Ephemerovirus, Hapavirus, Ledantevirus, Lyssavirus, Novirhabdovirus, Nucleorhabdovirus, Perhabdovirus, Sigmavirus, Sprivivirus, Sripuvirus, Tibrovirus, Tupavirus, Varicosavirus, Vesiculovirus. Non-limiting examples of preferred Rhabdovirus species include, but are not limited to, viral hemorrhagic septicemia virus (VHSV), vesicular stomatitis virus (VSV), and rabies virus (RABV).

In some embodiments, the non-alphavirus RNA replicon is derived from a negative-strand RNA virus species belonging to the Paramyxoviridae family. In some embodiments, the non-alphavirus RNA replicon is derived from a Paramyxovirus virus species belonging to the Pneumovirinae subfamily or the Paramyxovirinae subfamily. In some embodiments, the non-alphavirus RNA replicon is derived from a virus species belonging to a Paramyxovirus genus selected from the group consisting of Aquaparamyxovirus, Avulavirus, Ferlavirus, Henipavirus, Metapneumovirus, Morbillivirus, Pneumovirus, Respirovirus, and Rubulavirus. Non-limiting examples of preferred Paramyxovirus species include, but are not limited to, human respiratory syncytial virus (hRSV, subgroup A), bovine respiratory syncytial virus (bRSV), human metapneumovirus (hMPV), bovine-human parainfluenza virus 3 (b/hPIV3), human parainfluenza virus 1 (hPIV1), recombinant bovine-human parainfluenza virus 3 (rB/HPIV3), Sendai virus (SeV), Andes virus (ANDV), Mumps virus (MuV), Simian virus 5 (SV5), and Measles virus (MeV).

In some embodiments, the non-alphavirus RNA replicon is derived from a positive-strand virus species belonging to the Togaviridae family or Flaviviridae family. In some embodiments, the non-alphavirus RNA replicon is derived from a virus species belonging to the Flaviviridae family such as, for example, viruses belonging to the genera Flavivirus and Pestivirus. Non-limiting examples of viruses belonging to the genus Flavivirus include yellow fever virus (YFV), Dengue fever virus, Japanese encephalitis virus (JEV), West Nile virus (WNV) and Zika virus. In some embodiments, at least one of the first and second RNA replicons is derived from yellow fever virus or Dengue fever virus. Virulent and avirulent flavivirus strains are both suitable. Non-limiting examples of preferred flavivirus strains include, but are not limited to, YFV (17D), DEN4 (814669 and derivatives), DEN2 (PDK-53), Kunjin virus (KUN), JEV (SA14-14-2), Murray Valley encephalitis virus (MVEV, with IRES attenuated), WNV (SCFV), Bovine viral diarrhea virus (BVDV) CP7, BVDV-SD1, BVDV-NADL, and classical swine fever virus (CSFV).

In some embodiments, the non-alphavirus RNA replicon is derived from a positive-strand virus species belonging to the Arteriviridae family, which can be a virus of the genus Arterivirus. Suitable arterivirus species include, but are not limited to, species of Equine arteritis virus (EAV), Porcine respiratory and reproductive syndrome virus (PRRSV), Lactate dehydrogenase elevating virus (LDV), Simian hemorrhagic fever virus (SHFV), and wobbly possum disease virus (WPDV).

In some embodiments, at least one of the first and second RNA replicons comprises a modified 5'-UTR with one or more nucleotide substitutions at position 1, 2, 4, or a combination thereof. In some embodiments, at least one of the nucleotide substitutions is a nucleotide substitution at position 1 of the modified 5'-UTR. In some embodiments, at least one of the nucleotide substitutions is a nucleotide substitution at position 2 of the modified 5'-UTR. In some embodiments, at least one of the nucleotide substitutions is a nucleotide substitution at position 4 of the modified 5'-UTR. In some embodiments, the nucleotide substitutions at position 2 of the modified 5'-UTR is a U→G substitution. In some embodiments, the nucleotide substitution at position 2 of the modified 5'-UTR is a U→A substitution. In some embodiments, the nucleotide substitution at position 2 of the modified 5'-UTR is a U→C substitution.

In some embodiments of the disclosure, a part or the entire coding sequence for one or more viral structural proteins is absent and/or modified in the RNA replicon disclosed herein. Thus, in some particular embodiments, the RNA replicon as disclosed herein includes a modified 5-'UTR and is devoid of at least a portion of a nucleic acid sequence encoding one or more viral structural proteins, for example, devoid of the first one, two, three, four, five, six, seven, eight, nine, ten, or more nucleotides of the nucleic acid sequence encoding the viral structural proteins. In some embodiments, the modified RNA replicon can be devoid of about 10%, 20%, 30%, 40%, 50%, 60%, 70%, 80%, 90%, 95%, or more of the sequence encoding one or more of the structural polypeptides E1, E2, E3, 6K, and capsid protein C, or one or more other sequences encoding structural polypeptides. In some embodiments, the modified RNA replicon is devoid of a substantial portion of or the entire sequence encoding one of or more of the structural polypeptides E1, E2, E3, 6K, and capsid protein C, or one or more other sequences encoding structural polypeptides. As used herein, a "substantial portion" of a nucleic acid sequence encoding a viral structural protein comprises enough of the nucleic acid sequence encoding the viral structural protein to afford putative identification of that protein, either by manual evaluation of the sequence by one skilled in the art, or by computer-automated sequence comparison and identification using algorithms such as BLAST (see, for example, Karlin & Altschul, 1993, supra). In some embodiments, the modified RNA replicon is devoid of at least part of or of the entire sequence encoding one or more of the structural polypeptides E1, E2, E3, or of any combination or sub-combination of them. The modified RNA replicon can also be devoid of at least a portion of or of the entire sequence of protein 6K, and/or capsid protein C.

Viral Capsid Enhancer Sequences

In some embodiments disclosed herein, at least one of the first and second RNA replicons is a modified alphavirus replicon comprising one or more RNA stem-loops in a structural element of a viral capsid enhancer.

Some viruses have sequences capable of forming one or more stem-loop elements/structures which can be used, for example, in a heterologous viral genome for enhancing translation of a coding sequence located downstream thereto. For example, the subgenomic mRNA of Sindbis virus has a stable RNA hairpin loop located downstream of the wild type AUG initiator codon for the virus capsid protein (e.g., capsid enhancer). This stem-loop RNA structure is often referred to as the Downstream LooP (or DLP motif). The DLP structure was first characterized in Sindbis virus (SINV) 26S mRNA and also detected in Semliki Forest virus (SFV). Recently, similar DLP structures have been reported to be present in at least 14 other members of the Alphavirus genus including New World (MAYV, UNAV, EEEV (NA), EEEV (SA), AURAV) and Old World (SV, SFV, BEBV, RRV, SAG, GETV, MIDV, CHIKV, ONNV) members. The predicted structures of these Alphavirus 26S mRNAs were constructed based on SHAPE (selective 2'-hydroxyl acylation and primer extension) data (Toribio et al., Nucleic Acids Res. May 19; 44(9):4368-80, 2016), the content of which is hereby incorporated by reference). In the case of Sindbis virus, the DLP motif is found in the first ~150 nucleotides of the Sindbis subgenomic RNA. The hairpin is located downstream of the Sindbis capsid AUG initiation codon (AUG at nucleotide 50 of the Sindbis subgenomic RNA) and results in stalling a ribosome such that the correct capsid gene AUG is used to initiate translation. Because the hairpin causes ribosomes to pause eIF2α is not required to support translation initiation. Without being bound by any particular theory, it is believed that placing the DLP motif upstream of a coding sequence for any gene of interest (GOI) typically results in a fusion-protein of N-terminal capsid amino acids that are encoded in the hairpin region to the GOI-encoded protein because initiation occurs on the capsid AUG not the GOI AUG. In addition, unmodified RNA replicons are often sensitive to the initial innate immune system state of cells they are introduced into. If the cells/individuals are in a highly active innate immune system state, the RNA replicon performance (e.g., replication and expression of a GOI) can be negatively impacted. By engineering a DLP to control initiation of protein translation, particularly of non-structural proteins, the impact of the pre-existing activation state of the innate immune system to influence efficient RNA replicon replication is removed or lessened. The result is more uniform expression of the GOI that can impact vaccine efficacy or therapeutic impact of a treatment. Further information regarding alphavirus DLP can be found in, for example, U.S. patent application Ser. No. 15/831,230. In some embodiments, the viral capsid enhancer comprises a downstream loop (DLP) motif of the virus species, and wherein the DLP motif comprises at least one of the one or more RNA stem-loops. For example, in some embodiments, the viral capsid enhancer comprises a nucleic acid sequence exhibiting at least 80%, at least 85%, at least 90%, at least 95%, at least 96%, at least 97%, at least 98%, at least 99%, or 100% sequence identity to any one or more of SEQ ID NOs: 2-9. In some embodiments, the viral capsid enhancer comprises a nucleic acid sequence exhibiting about 80%, 85%, 90%, 95%, 96%, 97%, 98%, 99%, 100%, or a range between any two of these values, sequence identity to any one or more of SEQ ID NOs: 2-9. In some embodiments, the nucleic acid sequence exhibits at least 95% sequence identity to any one or more of SEQ ID NOs: 2-9.

In some embodiments, either one or both of the first and second RNA replicons is a modified alphavirus replicon comprising at least about 50, about 75, about 100, about 150, about 200, about 300 or more nucleotides from the 5' coding sequence for a viral capsid protein. In some embodiments, the viral capsid enhancer is derived from a capsid gene of an alphavirus species selected from the group consisting of Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu virus (NDUV), and Buggy Creek virus (BCRV). In some particular embodiments, the viral capsid enhancer is derived from a capsid gene of a Sindbis virus species or a Semliki Forest virus species. In yet some particular embodiments, the viral capsid enhancer is derived from a capsid gene of a Sindbis virus species. Additionally, one of ordinary skill in the art will appreciate that modifications may be made in the 5' coding sequences from the viral capsid protein without substantially reducing its enhancing activities (see, e.g., Frolov et al., *J. Virology* 70:1182, 1994; Frolov et al., J. Virology 68:8111, 1994). Preferably, such mutations substantially preserve the RNA hairpin structure formed by the 5' capsid coding sequences.

In some embodiments, the viral capsid enhancer sequence does not contain all of the 5' coding sequences of the viral capsid protein that are upstream of the hairpin structure. In some embodiments, the viral capsid enhancer sequence may encode all or part of the capsid protein. Accordingly, in some embodiments disclosed herein, the capsid enhancer region will not encode the entire viral capsid protein. In some embodiments, the viral capsid enhancer sequence will encode an amino terminal fragment from the viral capsid protein. In those embodiments in which an otherwise functional capsid is encoded by the capsid enhancer sequence, it may be desirable to ablate the capsid autoprotease activity.

In some embodiments, the viral capsid enhancer sequence included in the RNA replicons of the disclosure may be of any other variant sequence such as, for example, a synthetic sequence or a heterologous sequence, that can form an RNA hairpin functionally or structurally equivalent to one or more of the RNA stem-loops predicted for a viral capsid enhancer and which can act to enhance translation of RNA sequences operably linked downstream thereto (e.g., coding sequence for a gene of interest).

In some embodiments, at least one of the first and second RNA replicons is a modified alphavirus replicon that includes the coding sequence for at least one, at least two, at least three, or at least four heterologous non-structural proteins. In some embodiments, the modified alphavirus replicon includes the coding sequence for a heterologous non-structural protein nsP3. In some embodiments, the heterologous non-structural protein nsP3 is a Chikungunya virus (CHIKV) nsP3 or a Sindbis virus (SINV) nsP3. In some embodiments, at least one of the first and second antigens is expressed under control of a 26S subgenomic promoter or a variant thereof. In some embodiments, at least one of the first and second antigens is expressed under control of an alphavirus 26S subgenomic promoter or a variant thereof. In some embodiments, the 26S subgenomic promoter is a SINV 26S subgenomic promoter, RRV 26S subgenomic promoter, or a variant thereof.

Arteriviruses

The arteriviruses (Family Arteriviridae, Genus Arterivirus) encompass an important group of enveloped, single-stranded, positive-sense RNA viruses which infect domestic and wild animals. Arteriviruses share a similar genome organization and replication strategy to that of members of the family Coronaviridae (genera Coronavirus and Torovirus), but differ considerably in their genetic complexity, genome length, biophysical properties, size, architecture, and structural protein composition of the viral particles (e.g., virion). Currently, the Arterivirus genus is considered to include equine arteritis virus (EAV), porcine reproductive and respiratory syndrome virus (PRRSV), lactate dehydrogenase-elevating virus (LDV) of mice, simian hemorrhagic fever virus (SHFV), and wobbly possum disease virus (WPDV). Recent studies have reported that the newly identified wobbly possum disease virus (WPDV) also belongs to the Arterivirus genus.

A typical arterivirus genome varies between 12.7 and 15.7 kb in length but their genome organization is relatively consistent with some minor variations. The arterivirus genome is a polycistronic positive strand RNA, with 5' and 3' non-translated regions (NTRs) that flank an array of 10-15 known ORFs. The large replicase ORFs 1a and 1b occupy the 5'-proximal three-quarters of the genome, with the size of ORF1a being much more variable than that of ORF1b. Translation of ORF1a produces replicase polyprotein (pp) 1a, whereas ORF1b is expressed by −1 programmed ribosomal frameshifting (PRF), which C-terminally extends pp1a into pp1ab. In addition, a short transframe ORF has been reported to overlap the nsp2-coding region of ORF1a in the +1 frame and to be expressed by −2 PRF. The 3'-proximal genome part has a compact organization and contains 8 to 12 relatively small genes, most of which overlap with neighboring genes. These ORFs encode structural proteins and are expressed from a 3'-co-terminal nested set of subgenomic mRNAs. The organization of these ORFs is conserved, but downstream of ORF1b, SHFV and all recently identified SHFV-like viruses contain three or four additional ORFs (~1.6 kb) that may be derived from an ancient duplication of ORFs 2-4. Together with the size variation in ORF1a, this presumed duplication explains the genome size differences among arteriviruses.

With regard to equine arteritis virus (EAV), the wild-type EAV genome is approximately 12.7 kb in size. The 5' three fourths of the genome codes for two large replicase proteins 1a and 1ab; the amino acid sequences of the two proteins are N-terminally identical but due to a ribosomal frameshift the amino acid sequence of the C-terminal region of 1ab is unique. The 3' one quarter of the EAV genome codes for the virus's structural protein genes, all of which are expressed from subgenomic RNAs. The subgenomic RNAs form a nested set of 3' co-terminal RNAs that are generated via a discontinuous transcriptional mechanism. The subgenomic RNAs are made up of sequences that are not contiguous with the genomic RNA. All of the EAV subgenomic RNAs share a common 5' leader sequence (156 to 221 nucleotides in length) that is identical to the genomic 5' sequence. The leader and body parts of the subgenomic RNAs are connected by a conserved sequence termed a transcriptional-regulatory sequence (TRS). The TRS is found on the 3' end of the leader (leader TRS) as well as in the subgenomic promoter regions located upstream of each structural protein gene (body TRS). Subgenomic RNAs are generated as the negative strand replication intermediate RNA is transcribed. As transcription occurs, the replication complex pauses as it comes to each body TRS and then the nascent negative strand RNA becomes associated with the complementary positive strand leader TRS where negative strand RNA transcription continues. This discontinuous transcription mechanism results in subgenomic RNA with both 5' and 3' EAV conserved sequences. The negative strand subgenomic RNAs then become the template for production of the subgenomic positive sense mRNA.

Infectious cDNA clones, representing the entire genome of EAV, have been reported (van Dinten 1997; de Vries et al., 2000, 2001; Glaser et al., 1999) and they been used to study EAV RNA replication and transcription for nearly two decades (van Marle 1999, van Marle 1999a, Molenkamp 2000, Molenkamp 2000a, Pasternak 2000, Tijms 2001, Pasternak 2001, Pasternak 2003, Pasternak 2004, van den Born 2005, Beerens & Snijder 2007, Tijms 2007, Kasteren 2013). In addition, infectious clones have been generated that contain the chloramphenicol acetyltransferase (CAT) gene inserted in place of ORF2 and ORF7 and CAT protein was shown to be expressed in cells electroporated with those RNAs (van Dinten 1997, van Marle 1999). Modifications of the infectious clone via site directed mutagenesis and deletion of the structural protein gene regions has been used to determine the requirement for each structural gene in support of RNA replication (Molenkamp 2000). The study reported by Molenkamp 2000 concluded that the structural genes are not required to support RNA replication. Analysis of sequence homology requirements for TRS activity in subgenomic RNA production was conducted and used to better define how discontinuous transcription mechanistically occurs (van Marle 1999, Pasternak 2000, Pasternak 2001, Pasternak 2003, van den Born 2005) and defective interfering RNAs have been used to understand the minimal genomic sequences required for replication and packaging of RNA into virus particles (Molenkamp 2000a). Further information in this regard can be found in, for example, U.S. patent application Ser. No. 15/486,131, which is hereby incorporated by reference in its entirety.

In some embodiments disclosed herein, at least one of the first and second RNA replicons is derived from an arterivirus species. Suitable arterivirus species includes Equine arteritis virus (EAV), Porcine respiratory and reproductive syndrome virus (PRRSV), Lactate dehydrogenase elevating virus (LDV), Simian hemorrhagic fever virus (SHFV), and wobbly possum disease virus (WPDV). In some embodiments disclosed herein, at least one of the first and second RNA replicons is derived from an arterivirus species selected from the group consisting of Equine arteritis virus (EAV), Porcine respiratory and reproductive syndrome virus (PRRSV), Lactate dehydrogenase elevating virus (LDV), and Simian hemorrhagic fever virus (SHFV). In some embodiments, the arterivirus RNA replicon is derived from an Equine arteritis virus (EAV). Virulent and avirulent arterivirus strains are both suitable. Non-limiting examples of preferred arterivirus strains include, but are not limited to, EAV-virulent Bucyrus strain (VBS), LDV-Plagemann, LDV-C, PRRSV-type 1, and PRRSV-type 2. Exemplary preferred EAV strains include, but are not limited to, EAV VB53, EAV ATCC VR-796, EAV HK25, EAV HK116, EAV ARVAC MLV, EAV Bucyrus strain (Ohio), modified EAV Bucyrus, avirulent strain CA95, Red Mile (Kentucky), 84KY-A1 (Kentucky), Wroclaw-2 (Poland), Bibuna (Switzerland), and Vienna (Australia). Non-limiting preferred examples of PRRSV strains include PRRSV LV4.2.1, PRRSV 16244B, PRRSV HB-1(sh)/2002, PRRSV HB-2(sh)/2002, PRRSV HN1, PRRSV SD 01-08, PRRSV SD0802, PRRSV SD0803, PRRSV VR2332. Non-limiting preferred examples of SHFV strains and variants include SHFV variants SHFV-krtg1 a and -krtg1b (SHFVkrtg1a/b), SHFVkrtg2a/b (GenBank accession #JX473847 to JX473850), SHFV-LVR, the SHFV prototype variant LVR 42-0/M6941 (NC 003092), SHFV-krc1 and SHFVkrc2 from Kibale red colobus (HQ845737 and HQ845738, respectively). Other non-limiting examples of preferred arteriviruses include PRRSV-Lelystad, the European (type 1) type strain (M96262); PRRSVVR2332, the North American (type 2) type strain (U87392); EAV-Bucyrus (NC 002532); EAV-s3685 (GQ903794); LDV-P, the Plagemann strain (U15146); and LDV-C, the neurovirulent type C strain (L13298).

In some embodiments, the first and second RNA replicons are derived from the same arterivirus species or from two different arterivirus species. In some embodiments, the first RNA replicon is derived from an arterivirus and the second RNA replicon is derived from a non-arterivirus species. In some embodiments, the first RNA replicon is derived from an arterivirus and the second RNA replicon is derived from an alphavirus. In some embodiments, the first RNA replicon is an unmodified RNA replicon derived from an arterivirus species. In some embodiments, the first RNA replicon is a modified RNA replicon derived from an arterivirus species.

In some embodiments disclosed herein, the first RNA replicon is an RNA replicon derived from an alphavirus species and the second RNA replicon is an RNA replicon derived from an arterivirus species. In certain embodiments, the first RNA replicon is an unmodified RNA replicon derived from an alphavirus species. In other embodiments, the first RNA replicon is a modified RNA replicon derived from an alphavirus species.

In some embodiments disclosed herein, the methods of the disclosure further include one or more subsequent boosting administrations. In some embodiments, the methods of the disclosure further include at least 2, at least 3, at least 4, at least 5, or at least 10 consecutive boosting administrations or any number administration therebetween. In some embodiments, the subsequent boosting administrations are performed in gradually increasing dosages over time. In some embodiments, the subsequent boosting administrations are performed in gradually decreasing dosages over time.

In some embodiments, one or more of the priming composition and the boosting composition further comprises a pharmaceutically acceptable carrier. As used herein, the term "pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use. In some embodiments, a pharmaceutically acceptable carrier is as simple as water, but it can also include, for example, a solution of physiological salt concentration or saline. It can also be a lipid nanoparticle. Suitable materials include polyamidoamine (PAMAM) C12 dendrimers, and/or 1,2-dimyristoiyl-sn-glycero-3-phosphoethanolamine-N-[methoxy(polyethylene glycol)-2000]. Polyethleneimine (PEI) and/or G5 and G9 NH2 PAMAM dendrimers can also be used. In some embodiments, a pharmaceutically acceptable carrier can be, or may include, stabilizers, diluents and buffers. Suitable stabilizers are for example SPGA, carbohydrates (such as dried milk, serum albumin or casein) or degradation products thereof. Suitable buffers are for example alkali metal phosphates. Diluents include water, aqueous buffers (such as buffered saline), alcohols and polyols (such as glycerol). For administration to animals or humans, the composition according to the present application can be given inter alia parenterally, intranasally, by spraying, intradermally, subcutaneously, orally, by aerosol or intramuscularly.

In some embodiments, the first and the second RNA replicon each comprises at least one expression cassette comprising a promoter operably linked to a coding sequence for a gene of interest (GOI). As used herein, the term "expression cassette" refers to a construct of genetic material that contains coding sequences for a protein or functional RNA operably linked to expression control elements, such as a promoter, with enough regulatory information to direct proper transcription and/or translation of the coding sequences in a recipient cell, in vivo and/or ex vivo.

The term "operably linked", as used herein, denotes a functional linkage between two or more sequences. For example, an operable linkage between a polynucleotide of interest and a regulatory sequence (for example, a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

Techniques for operably linking two or more sequences of DNA together are familiar to one of skill in the art, and such techniques have been described in a number of texts for standard molecular biological manipulation (see, for example, Maniatis et al., "*Molecular Cloning: A Laboratory Manual*" 2nd ed. Cold Spring Harbor Laboratory Press, Cold Spring Harbor, N.Y.; and Gibson et al., *Nature Methods* 6:343-45, 2009).

In some embodiments disclosed herein, the RNA replicons disclosed herein can include more than one expression cassette. In principle, the RNA replicons disclosed herein can generally include any number of expression cassettes. In some particular embodiments, the RNA replicons comprise at least two, three, four, five, or six expression cassettes. In some embodiments, at least one of the one or more expression cassettes is operably positioned downstream to a transcriptional regulatory sequence (TRS) of an arterivirus RNA replicon, wherein the TRS is selected from the group consisting of TRS1, TRS2, TRS3, TRS4, TRS5, TRS6, and TRS7. In some particular embodiments, at least one of the one or more expression cassettes is operably positioned downstream of the TRS7 of an arterivirus RNA replicon.

In some embodiments, the coding sequence of the GOI is optimized for expression at a level higher than the expression level of a reference coding sequence. In some embodiments, the reference coding sequence is a sequence that has not been optimized. In some embodiments, the optimization of the GOI coding sequence can include codon optimization. With respect to codon-optimization of nucleotide sequences, degeneracy of the genetic code provides the possibility to substitute at least one base of the protein encoding sequence of a gene with a different base without causing the amino acid sequence of the polypeptide produced from the gene to be changed. Hence, the polynucleotides of the present application may also have any base sequence that has been changed from any polynucleotide sequence described herein by substitution in accordance with degeneracy of the genetic code. References describing codon usage are readily publicly available. In some further embodiments of the disclosure, polynucleotide sequence variants can be produced for a variety of reasons, e.g., to optimize codon expression for a particular host (e.g., changing codons in the arterivirus mRNA to those preferred by other organisms such as human, hamster, mice, or monkey).

In some embodiments disclosed herein, the GOI can encode an amino acid sequence of a polypeptide. The polypeptide can generally be any polypeptide, and can be, for example a therapeutic polypeptide, a prophylactic polypeptide, a diagnostic polypeptide, a nutraceutical polypeptide, an industrial enzyme, and a reporter polypeptide. In some embodiments, the GOI encodes a polypeptide selected from the group consisting of an antibody, an antigen, an immune modulator, and a cytokine. In some embodiments, the GOI encodes a polypeptide selected from the group consisting of a therapeutic polypeptide, a prophylactic polypeptide, a diagnostic polypeptide, a nutraceutical polypeptide, an industrial enzyme, and a reporter polypeptide.

In some embodiments, the RNA replicons disclosed herein further comprise a coding sequence for a proteolytic cleavage site operably linked downstream to the third nucleotide sequence and upstream to the coding sequence for the GOI. Generally, any proteolytic cleavage site known in the art can be incorporated into the polynucleotides and RNA replicons of the disclosure and can be, for example, proteolytic cleavage sequences that are cleaved post-production by a protease. Further suitable proteolytic cleavage sites also include proteolytic cleavage sequences that can be cleaved following addition of an external protease. In some embodiments, RNA replicons disclosed herein further comprise a coding sequence for an autoprotease peptide operably linked downstream to the third nucleotide sequence and upstream to the coding sequence for the GOI. As used herein the term "autoprotease" refers to a "self-cleaving" peptide that possesses autoproteolytic activity and is capable of cleaving itself from a larger polypeptide moiety. First identified in the foot-and-mouth disease virus (FMDV), which is a member of the picornavirus group, several autoproteases have been subsequently identified such as, for example, "2A like" peptides from equine rhinitis A virus (E2A), porcine teschovirus-1 (P2A) and Thosea asigna virus (T2A), and their activities in proteolytic cleavage have been shown in various in vitro and in vivo eukaryotic systems. As such, the concept of autoproteases is available to one of skill in the art with many naturally occurring autoprotease systems having been identified. Well-studied autoprotease systems include, but are not limited to, viral proteases, developmental proteins (e.g. HetR, Hedgehog proteins), RumA autoprotease domain, UmuD, etc.). Non-limiting examples of autoprotease peptides suitable for the compositions and methods of the present disclosure include the peptide sequences from porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2a (BmCPV2A), a Flacherie Virus 2A (BmIFV2A), or a combination thereof.

Compositions of the Disclosure

Some embodiments disclosed herein relate to a composition which includes: a priming composition comprising a first RNA replicon which encodes a first antigen; and a boosting composition comprising a second RNA replicon which encodes a second antigen, wherein the first and second RNA replicons are different from each other. In some embodiments, amino acid sequences of the first and the second antigens are homologous to each other. In some embodiments, the first and the second antigens are identical to each other. In some embodiments, the first and the second antigens comprise at least one cross-reactive antigenic determinant. In some embodiments, the composition is for inducing an immune response in a subject. In some embodiments, the first and the second antigens induce substantially the same immune response in the subject. The composition can be, for example, a prophylactic composition or a pharmaceutical composition comprising a pharmaceutically acceptable carrier, or a mixture thereof. In some embodiments, the compositions of the present application can be used as a vaccine.

Some embodiments disclosed herein relate to a composition which includes: a first nucleic acid sequence encoding a first RNA replicon which encodes a first antigen; and a second nucleic acid sequence encoding a second RNA replicon which encodes a second antigen, wherein the first and second RNA replicons are different from each other, wherein the first replicon and the second replicon comprises at least one expression cassette comprising a promoter operably linked to a coding sequence for a molecule of interest. In some embodiments, amino acid sequences of the first and the second antigens are homologous to each other. In some embodiments, the first and the second antigens are identical to each other. In some embodiments, the first and the second antigens comprise at least one cross-reactive antigenic determinant. In some embodiments, the amino acid sequence of the first antigen exhibits at least 80%, 85%, 90%, 95%, 96%, 97%, 98%, or 99% sequence identity to the amino acid sequence of the second antigen. In some embodiments, the composition is for producing a molecule of interest. In some embodiments, the molecule of interest is a polypeptide. The polypeptide can generally be any polypeptide, and can be, for example a therapeutic polypeptide, a prophylactic polypeptide, a diagnostic polypeptide, a nutraceutical polypeptide, an industrial enzyme, and a reporter polypeptide. In some embodiments, the molecule of interest is a polypeptide selected from the group consisting of an antibody, an antigen, an immune modulator, and a cytokine. In some embodiments, the molecule of interest is a polypeptide selected from the group consisting of a therapeutic polypeptide, a prophylactic polypeptide, a diagnostic polypeptide, a nutraceutical polypeptide, an industrial enzyme, and a reporter polypeptide.

Methods for Producing Molecules of Interest

The compositions and methods of the present disclosure can be used to produce (e.g., express) a molecule of interest such as, e.g., a polypeptide, encoded in an open reading frame of a gene of interest (GOI) as disclosed herein. Thus, the present application further provides compositions and methods for producing a molecule of interest such as, e.g., a polypeptide. Further information in this regard can be found in, for example, U.S. patent application Ser. Nos. 15/486,131; 15/723,658, and 15/831,230.

Accordingly, some embodiments relate to methods for producing a polypeptide of interest in a subject, including sequentially administering to the subject the first and the second RNA replicons according to any one of the aspects and embodiments.

The methods and compositions disclosed herein can be used, for example, with subjects that are important or interesting for aquaculture, agriculture, animal husbandry, and/or for therapeutic and medicinal applications, including production of polypeptides used in the manufacturing of vaccines, pharmaceutical products, industrial products, chemicals, and the like. In some embodiments, the compositions and methods disclosed herein can be used with subjects that are natural hosts of alphaviruses, such as rodents, mice, fish, birds, and larger mammals such as humans, horses, pig, monkey, and apes as well as invertebrates. Particularly preferred species, in some embodiments of the application, are vertebrate animal species and invertebrate animal species. In principle, any animal species can be generally used and can be, for example, mammalian species such as human, horse, pig, primate, mouse, ferret, rat, cotton rat, cattle, swine, sheep, rabbit, cat, dog, goat, donkey, hamster, or buffalo. In some embodiments, the subject is an avian species, a crustacean species, or a fish species. In some embodiments, the avian species is an avian species for food consumption. Non-limiting examples of suitable avian species include chicken, duck, goose, turkey, ostrich, emu, quail, pigeon, swan, peafowl, pheasant, partridge, and guinea fowl. The term "crustacean" as used herein includes all crustacean species, for example those commonly referred to as "shrimp," "lobsters," "crawfish," and "crabs," such as *Penaeus, Litopenaeus, Marsupenaeus, Fenneropenaeus*, and *Farfantepenaeus*. In some embodiments, the crustacean species are shrimp species, particularly those that are raised in aquaculture such as *Litopenaeus vannamei, Penaeus vannamei, Penaeus styllirostris, Penaeus monodon, Pandalus borealis, Acetes japonicas, Trachysalambria curvirostris*, and *Fenneropenaeus chinensis*. In some embodiments, the fish are ornamental fish or fish species used in aquaculture for consumption such as, eel, salmon, trout, carp, catfish, bass, and tilapia. In some embodiments, the fish species is in the Salmonidae family.

Techniques for transforming or transfecting a wide variety of the above-mentioned subjects are known in the art and described in the technical and scientific literature.

All publications and patent applications mentioned in this disclosure are herein incorporated by reference to the same extent as if each individual publication or patent application was specifically and individually indicated to be incorporated by reference.

It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure and are to be included within the spirit and purview of this application.

EXAMPLES

Additional alternatives are disclosed in further detail in the following examples, which are not in any way intended to limit the scope of the claims.

Example 1

Increased Immune Response Following Heterologous Prime-Boost Using Different RNA Replicons This Example summarizes the experiments illustrating the induction of an immune response following heterologous prime-boost immunization performed with RNA replicons which activate an immune system of a subject through immunologically distinct mechanisms. As described above, heterologous prime-boost immunization is believed to generate enhanced immune responses through (1) avoidance of anti-vector immunity, and (2) differential and synergistic activation of the immune response. While heterologous prime-boosts schedules have demonstrated efficacy using distinct platforms for delivery, this approach has been unavailable through the rational engineering of replicons. To date, replicons that differentially engage the immune system have not been employed to improve either T or B cell responses. In addition, the use of two distinct systems to avoid anti-vector responses against replicons that encode for a therapeutic protein has not been previously possible as a method to enhance the magnitude or durability of protein expression.

Described herein is the use of two different fully synthetic replicon systems as a means of enhancing the immune response in a heterologous prime-boost format. Although using two different systems for heterologous-prime boost has been effective for other vaccines due to avoidance of anti-vector immunity and differential activation of the immune system, this has not formerly been possible or demonstrated using replicons. The reasons for this are two-fold. First, alphavirus replicons are the only replicon system available currently in use, and the novel engineering of EAV allowed for this method of immunization or protein administration. Second, the lack of rational engineering within the same viral family to significantly alter the mechanism of immune activation between two different replicons to drive differential immune responses in a heterologous prime-boost format has not been demonstrated.

In the experiments described in this Example, RNA replicons derived from two different viruses: an arteritis virus (Equine arteritis virus—EAV) and an alphavirus (Venezuelan equine encephalitis virus—VEEV), were used as representative of the heterologous RNA replicon prime-boost approach. Recombinant EAV-based and VEEV-based RNA replicons have been designed and subsequently used to vaccinate mice in a heterologous prime-boost vaccination regime. As described in more detail below, these recombinant RNA replicons have been tested in vivo in mouse models and demonstrated a differentiated and enhanced immune response in comparison with control animals receiving a homologous prime-boost regime. For example, Applicant has demonstrated in saline formulations that a heterologous prime-boost regime produces superior T cell response following a boosting step when compared to EAV-EAV immunization or VEEV-VEEV immunization using a hemagglutinin (HA) antigen derived from Influenza A/Vietnam/1203/2003 (H5N1) strain.

To analyze the effect of heterologous prime-boosts on the immunogenicity of replicons, mice were immunized with combinations of either EAV replicon or a VEE replicon containing a Downstream LooP sequence (or DLP motif). Each replicon includes coding sequences for hemagglutinin (HA) from Influenza A/Vietnam/1203/2004 (H5N1). In these experiments, BALB/c mice were immunized with a dose of 15 μg formulated in saline and injected intramuscularly at intervals of 4 weeks. Fourteen days following the final injection, spleens and serum were collected to analyze the immune responses to HA. A summary of the results of these experiments is presented in FIGS. 2A-2B.

As shown in FIG. 2A, splenocytes were stimulated with conserved T cell epitope (H-2 Kd: IYSTVASSL; SEQ ID NO: 1) and revealed a significant increase in IFN-γ-secreting CD8+ T cells in the group receiving a heterologous prime-boost regimen, where the priming composition includes an EAV replicon and the boosting composition includes a VEEV replicon, when compared to either homologously-primed group or single-dose group.

The above observation differed from animals that received a heterologous prime-boost regimen where the priming composition included a VEEV replicon and the boosting composition included an EAV replicon, demonstrating the differential effects of a heterologous prime-boost regime compared with a homologous prime-boost regimen. Without being bound by any particular theory, one possible explanation for the increased CD8+ T cell response in the heterologous EAV-VEEV administration group versus the homologous VEEV-VEEV group is a diminished anti-vector immunity to the viral non-structural proteins encoded by the replicon. As discussed above, anti-vector immunity would result in a more rapid clearance of cells expressing the replicon and thus result in restriction of the expressed antigen at boost.

The data presented above also suggests that the order of administration of each replicon has an effect on the T cell responses generated. Specifically, a heterologous prime-boost schedule with a VEEV-based replicon first followed by a EAV-based replicon did not generate the same frequency of IFNγ+ antigen-specific CD8+ T cells than, a heterologous prime-boost regimen with a EAV priming first followed by a VEEV boost. In agreement with the above observation, the order of administration has also been shown to give differential T cell responses in other heterologous prime-boost vaccine model systems. For example, for protection against malaria using viral-based vectors, priming with an Adenovirus-based vector encoding the malarial antigen ME.TRAP, followed by a boost with a modified Vaccinia Ankara based vector encoding the same antigen resulted in better T cell memory responses and enhanced protection than the reverse order of administration.

Figure 2A:
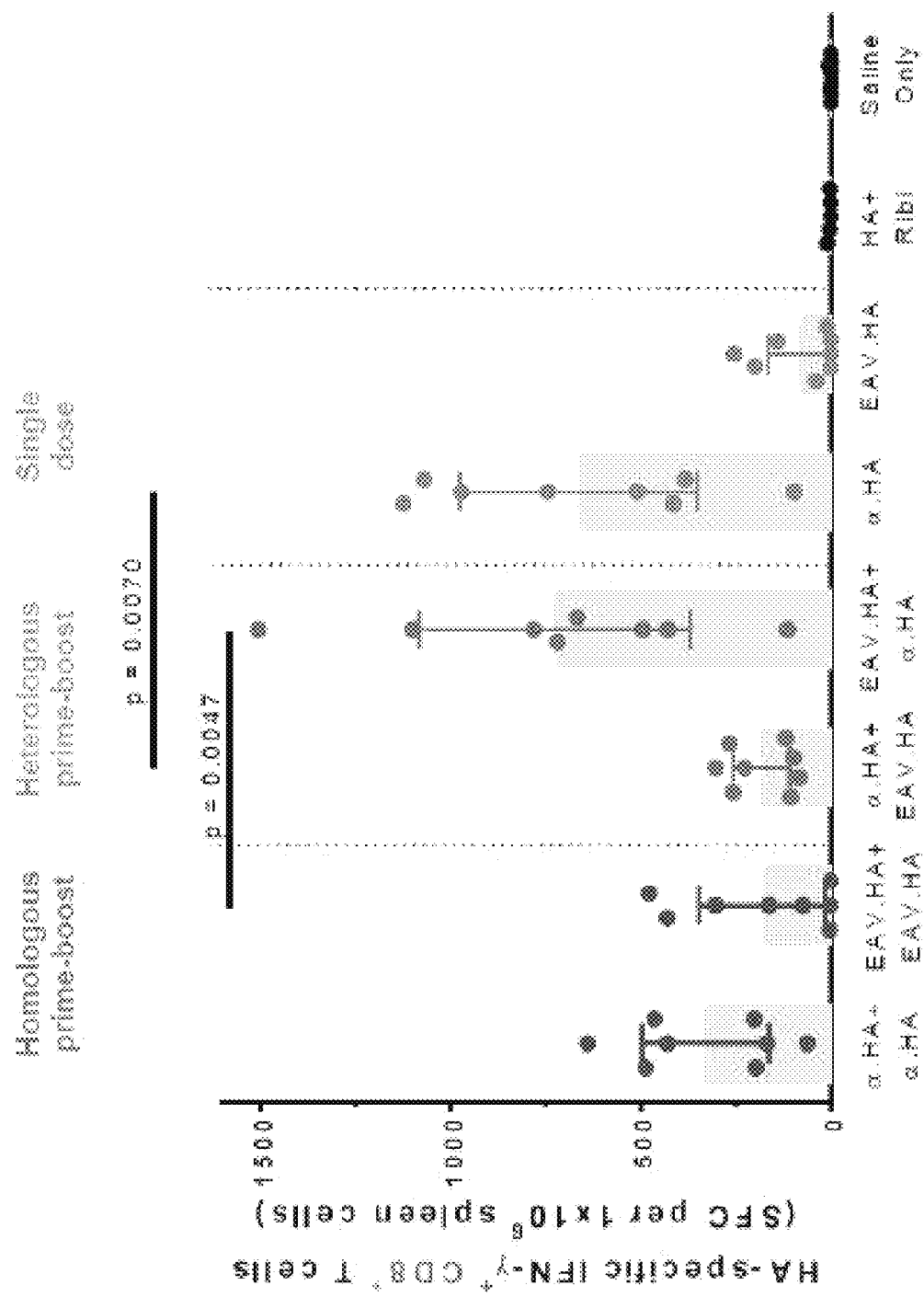
FIGS. 2A-2B schematically summarize the results of experiments performed to analyze immune responses in mice after various prime-boosting schedules in accordance with some embodiments of the disclosure.
Figure 2B:
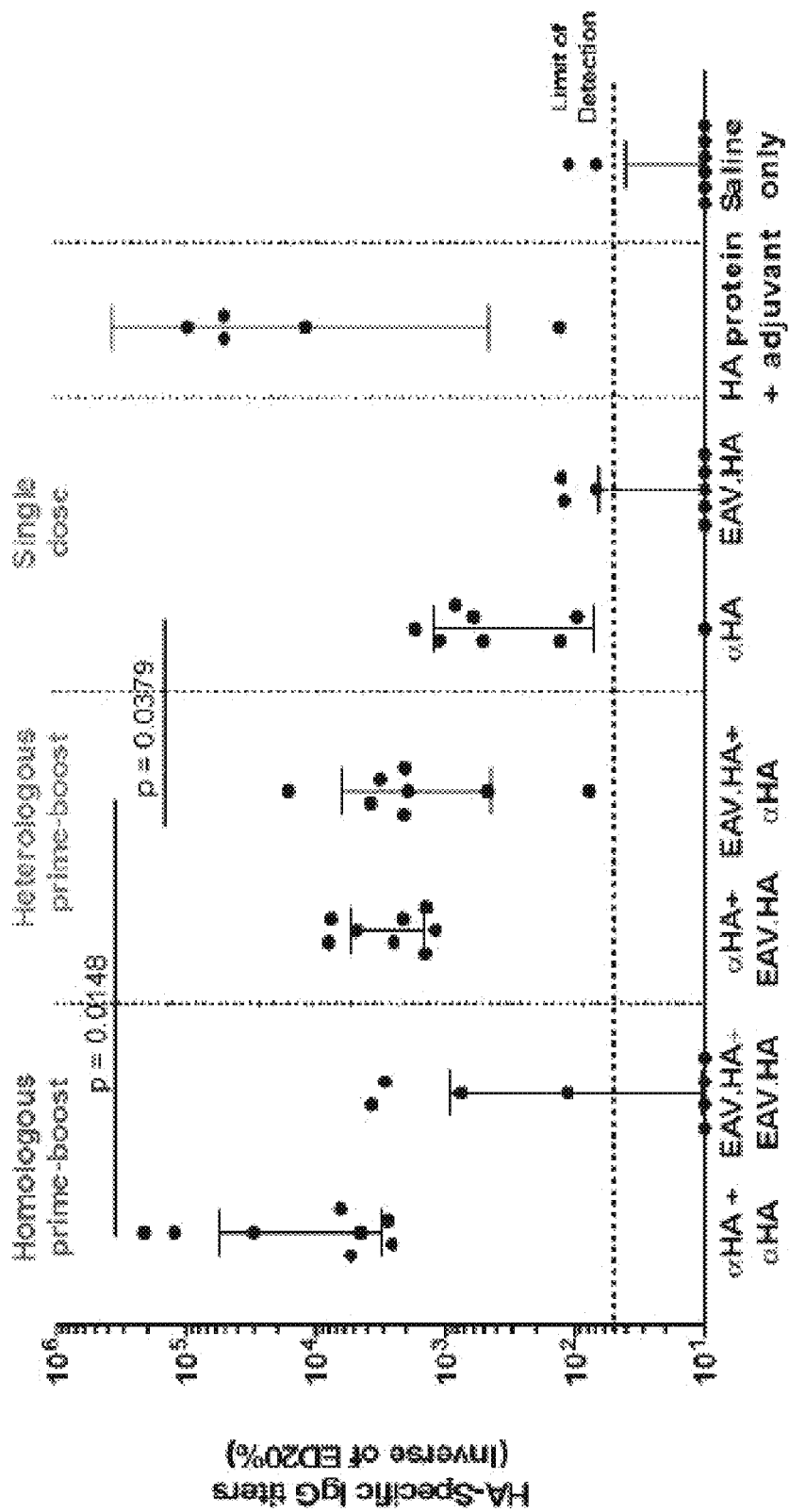

As shown in FIG. 2B, B cell responses in various heterologous prime-boost regimens were also examined. Serum from animals were collected at fourteen (14) days post the final injection and assessed for HA-specific total IgG responses. In contrast to elevated CD8+ T cell responses, B cell responses from animals that received a heterologous EAV-VEEV prime-boost regimen showed a marginal and slightly decreased level of antigen-specific total IgG when compared to the VEEV-VEEV homologous regimen group. However, B cell responses observed in both heterologous prime-boost groups (i.e. EAV-VEEV and VEEV-EAV) were significantly higher than animals receiving a single dose. In this manner, heterologous prime-boost can be used to elicit B cell responses with significantly improved effector CD8+ T cell responses.

It was unexpected that T cell responses at 14 days post-boost were improved using two different replicons in contrast to a homologous prime-boost regime. However, any differences in immune responses were conceptually unexpected since this has not been attempted previously. Specifically, it was unexpected that a VEEV replicon prime followed by an EAV replicon boost yielded an inferior T cell response to an EAV replicon prime and VEEV replicon boost. Furthermore, it was also unexpected that heterologous prime-boost enhanced both T and B cell responses when compared to EAV-EAV replicon homologous prime-boost, but only superior T cell responses when compared with an VEEV-VEEV replicon homologous prime-boost. Finally, in contrast to other demonstrations of heterologous prime-boosts, the observation that mRNAs capable of self-amplification, which are chemically similar, could differentially affect downstream immune responses following administration is also unexpected.

In particular, since a prime immunization with an EAV-based replicon followed by a boost immunization with an alphavirus-based replicon demonstrated the best T cell responses, additional experiments are also performed to prime the immune system with an EAV-based replicon followed by a boost immunization using each of the alphavirus-based replicons listed below in Table 1.

TABLE 1

Non-limiting exemplary combinations of heterologous prime-boost regimens of the present disclosure.

| | Prime | Boost |
|---|---|---|
| 1 | EAV replicon | nt2 point mutant of the alphavirus replicon* |
| 2 | nt2 point mutant of the alphavirus replicon | EAV replicon |
| 3 | DLP motif-containing alphavirus replicon | nt2 point mutant of the alphavirus replicon |
| 4 | nt2 point mutant of the alphavirus replicon | DLP motif-containing alphavirus replicon |
| 5 | EAV replicon | CHIKV nsP3 variant alphavirus replicon |
| 6 | EAV replicon | SINV nsP3 variant alphavirus replicon |
| 7 | EAV replicon | RRV 26S promoter variant alphavirus |
| 8 | EAV replicon | SINV 26S promoter variant alphavirus |
| 9 | DLP motif-containing alphavirus replicon | CHIKV nsP3 variant alphavirus replicon |
| 10 | DLP motif-containing alphavirus replicon | SINV nsP3 variant alphavirus replicon |
| 11 | CHIKV nsP3 variant alphavirus replicon | DLP motif-containing alphavirus replicon |
| 12 | SINV nsP3 variant alphavirus replicon | DLP motif-containing alphavirus replicon |
| 13 | RRV 26S promoter variant alphavirus | DLP motif-containing alphavirus replicon |
| 14 | DLP motif-containing alphavirus replicon | RRV 26S promoter variant alphavirus |
| 15 | SINV 26S promoter variant alphavirus | DLP motif-containing alphavirus replicon |
| 16 | DLP motif-containing alphavirus replicon | SINV 26S promoter variant alphavirus |
| 17 | WT alphavirus replicon** | DLP motif-containing alphavirus replicon |
| 18 | DLP motif-containing alphavirus replicon | WT alphavirus replicon |

*alphavirus replicon comprising a modified 5'-UTR with a nucleotide substitution at position 2.
**Wild-type/unmodified alphavirus replicon.

Additional experiments are also performed to demonstrate the following: (1) superiority of the immune responses of EAV-VEEV or VEEV-EAV either in saline or LNP (cationic lipid nanoparticle) formulations, (2) superiority of two VEEV replicons with immunological mechanisms of immune activation, and (3) superiority of heterologous prime-boost in a therapeutic setting.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A method for inducing an immune response in a subject, comprising:
   administering to the subject at least one dose of a priming composition comprising a first RNA replicon which encodes a first antigen; and
   subsequently administering to the subject at least one dose of a boosting composition comprising a second heterologous RNA replicon which encodes a second antigen, wherein the first and second RNA replicons are different from each other, and
   the first RNA replicon is derived from equine arteritis virus (EAV) and the second RNA replicon is derived from an alphavirus species.

2. The method of claim 1, wherein the first and the second antigens comprise at least one cross-reactive antigenic determinant.

3. The method of claim 1, wherein the first RNA replicon activates an immune system of the subject through at least one immunological mechanism that is different from an immunological mechanism by which the second RNA replicon activates the immune system.

4. The method of claim 1, wherein the alphavirus species is selected from the group consisting of Eastern equine encephalitis virus (EEEV), Venezuelan equine encephalitis virus (VEEV), Everglades virus (EVEY), Mucambo virus (MUCV), Semliki forest virus (SFV), Pixuna virus (PIXV), Middleburg virus (MIDY), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABY), Kyzylagach virus (KYZV), Western equine encephalitis virus (WEEV), Highland J virus (HJV), Fort Morgan virus (FMV), Ndumu virus (NDUV), Salmonid alphavirus (SAV), and Buggy Creek virus (BCRV).

5. The method of claim 1, wherein at least one of the first and second RNA replicons comprises a modified 5'-UTR with one or more nucleotide substitutions at position 1, 2, 4, or a combination thereof.

6. The method of claim 5, wherein at least one of the one or more nucleotide substitutions is a nucleotide substitution at position 2 of the modified 5'-UTR.

7. The method of claim 6, wherein the nucleotide substitution at position 2 of the modified 5'-UTR is a U→G substitution.

8. The method of claim 1, wherein at least one of the first and second RNA replicons is a modified RNA replicon comprising a modified 5'-UTR and is devoid of at least a portion of a nucleic acid sequence encoding one or more viral structural proteins.

9. The method of claim 1, wherein the second RNA replicon is a modified alphavirus replicon comprising one or more RNA stem-loops in a structural element of a viral capsid enhancer or a variant thereof.

10. The method of claim 1, wherein the second RNA replicon is a modified alphavirus replicon comprising a coding sequence for a heterologous non-structural protein nsP3.

11. The method of claim 10, wherein the heterologous non-structural protein nsP3 is a Chikungunya virus (CHIKV) nsP3, a Sindbis virus (SINV) nsP3, or a variant thereof.

12. The method of claim 1, wherein at least one of the first and second antigens is expressed under control of a 26S sub genomic promoter or a variant thereof.

13. The method of claim 12, wherein the 26S subgenomic promoter is a SINV 26S subgenomic promoter, a RRV 26S subgenomic promoter, or a variant thereof.

14. The method of claim 1 wherein the alphavirus is derived from VEEV.

15. The method of claim 1 wherein the first RNA replicon and the second RNA replicon each comprise a sequence encoding a gene of interest.

16. The method of claim 15 wherein the gene of interest encodes a polypeptide that is an antigenic determinant to the subject.

17. The method of claim 1, wherein the method comprises administering two or more doses of the boosting composition to the subject.

18. The method of claim 1, wherein one or more of the priming composition and the boosting composition comprises a pharmaceutically acceptable carrier.

19. The method of claim 1, wherein the subject is an avian species, a crustacean species, or a fish species.

20. The method of claim 1, wherein the subject is a mammal.

21. The method of claim 1, wherein the subject is an aquatic animal or an avian species.

22. A method for delivering two RNA replicons into a subject, comprising
administering to the subject a first nucleic acid sequence encoding a first RNA replicon which encodes a first antigen; and
subsequently administering to the subject, a second nucleic acid sequence encoding a second heterologous RNA replicon which encodes a second antigen,
wherein the first and second RNA replicons are different from each other, and
the first RNA replicon is derived from equine arteritis virus (EAV) and the second RNA replicon is derived from an alphavirus species.

23. The method of claim 1, wherein one or more of the priming and boosting compositions comprise a pharmaceutically acceptable carrier comprising a lipid nanoparticle.

24. The method of claim 9, wherein the viral capsid enhancer comprises a nucleic acid sequence exhibiting at least 90% sequence identity to SEQ ID NO: 2.

* * * * *